United States Patent [19]

Hutchings et al.

[11] Patent Number: 5,770,750

[45] Date of Patent: Jun. 23, 1998

[54] ALKYD AND ARALKYD DERIVATIVES OF PHENOLIC POLYMERS

[75] Inventors: David A. Hutchings, Tucker; Rajan Hariharan, Duluth; Edward Lucas, Jr., Peachtree City; Syed A. Elahi, Woodstock, all of Ga.; Alan K. Randall, Delaware, Ohio; Kenneth Bourlier, Decatur, Ga.

[73] Assignee: Georgia-Pacific Resins, Inc., Atlanta, Ga.

[21] Appl. No.: 781,669

[22] Filed: Jan. 10, 1997

[51] Int. Cl.[6] .................................................. C07C 53/00
[52] U.S. Cl. .......................... 554/223; 252/321; 252/358; 554/172; 554/224; 554/227
[58] Field of Search .................... 554/223, 172, 554/224, 227; 252/321, 358

[56] References Cited

U.S. PATENT DOCUMENTS

| | | | |
|---|---|---|---|
| 3,267,154 | 8/1966 | Hokama | 260/619 |
| 3,379,708 | 4/1968 | Peacock et al. | 260/97.5 |
| 3,393,243 | 7/1968 | Cuscurida | 260/615 |
| 3,461,068 | 8/1969 | Peacock et al. | 252/8.5 |
| 3,733,365 | 5/1973 | Yeakey et al. | 260/624 |
| 4,595,743 | 6/1986 | Laughner | 528/73 |
| 4,895,681 | 1/1990 | Herrmann et al. | 252/321 |
| 4,962,186 | 10/1990 | Johnson, Jr. | 530/218 |
| 5,057,627 | 10/1991 | Edwards | 568/618 |
| 5,106,874 | 4/1992 | Porter et al. | 528/64 |
| 5,362,894 | 11/1994 | Handwerker et al. | 554/169 |
| 5,439,724 | 8/1995 | Rojek | 428/66.3 |
| 5,466,843 | 11/1995 | Cooper | 554/149 |

*Primary Examiner*—Terressa Mosley
*Attorney, Agent, or Firm*—Banner & Witcoff

[57] ABSTRACT

Phenolic aralkylation polymers modified by esterification with fatty acids, transesterification with glyceride oils, or other modifications to reactive hydroxyl moieties to improve the characteristics and properties of coating systems in which the modified materials are incorporated. At least a portion of the hydroxyl moieties of the polyol is esterified or otherwise modified. The hydroxyl moieties include those that have been "chain-extended," if desired.

36 Claims, No Drawings

ALKYD AND ARALKYD DERIVATIVES OF PHENOLIC POLYMERS

This invention is directed to alkyd and aralkyd derivatives of phenolic polyol polymers. In particular, the invention is directed to the products resulting from the esterification or similar modification of reactive hydroxyl moieties on the phenolic polymers. The invention also relates to the use of such modified phenolic polymers in, e.g., coating systems.

BACKGROUND OF THE INVENTION

Phenolic polyols are a common component of coating systems. Phenolics can be "cooked" with other components, such as drying oils, or can be cold blended with other components to produce coating systems.

Alkyd resins are commonly used in coating systems. Alkyd resins are formed through the incorporation of unsaturated fatty acid esters into polyester or polyurethane chain-extended polymer systems. The simplest alkyd polyesters are those based on reaction products of tri-glycerides of unsaturated fatty acids.

In early resins of this type used in coating applications, speed of cure (drying speed) was increased through thermal advancement ("cooking") of the resin and viscosity was reduced by incorporation of a solvent prior to use. Such resins comprise fatty acid tri-glycerides which have undergone some degree of coupling of their unsaturated linkages to generate higher molecular weight, cross linked systems. Generally speaking, this cross linking is accomplished thermally at high temperatures through free radical addition reactions or oxidatively. The latter process is promoted by incorporation of transition metal complexes capable of catalyzing the auto-oxidation of the allylic hydrogens associated with the unsaturated fatty acids to generate hydroperoxides and peroxides which are capable of facilitating cross-link formation between fatty acid double bonds by initiating free radical addition processes.

Later versions of alkyds are based on transesterified tri-glycerides. In these systems, a tri-glyceride is reacted with excess glycerol to generate a mixture of mono-, di-, and tri-glyceride, with the mono-glyceride component present in the largest amount. The resulting prepolymer is then reacted with di-acids or anhydrides, such as adipic acid, phthalic anhydride, or isophthalic acid, to produce chain-extended polyesters containing fatty acid ester side chains. Such polyesters are capable of undergoing relatively rapid cure in the presence of the aforementioned auto-oxidation catalyst systems.

The polymers also are capable of being modified through the incorporation of other polyols, i.e., diols, triols, tetraols, or higher order alcohols. In addition, transesterification may be carried out with polyols other than glycerol. One polyol of particular interest is pentaerythritol, which is a primary tetraol. This material can be esterified with fatty acids through transesterification with naturally occurring triglycerides of unsaturated fatty acids or through the direct esterification with unsaturated fatty acids, such as those found in commercial tall oil fatty acid streams. In the latter case, pentaerythritol can be reacted with 1, 2, or 3 fatty acid moieties and incorporated into an alkyd coating system.

Uralkyds are analogous to the polyester alkyds. Uralkyds are derived from substitution of di- or poly-isocyanate for a portion of the di-acid component to achieve chain extension or grafting. Uralkyds are produced from base alkyds having excess hydroxy functionality. The above-described polyols can be reacted at modest temperatures under catalysis with di-or poly-isocyanates to product urethane-linked coating systems having improved mechanical, environmental, and hydrolytic performance.

Phenolics are used to impart desirable characteristics, such as adhesion and corrosion resistance, to coating systems. However, phenolics are not without drawbacks. For example, phenolics typically have high viscosity, thus limiting their use in low VOC systems. Phenolics tend to darken with age, thus changing the color of the coating. Indeed, such a color change might "bleed through" subsequently-applied coating layers, thus reducing the suitability of a primer coat comprising a phenolic moiety.

Typical phenolics are the product of polymerization of a phenol with a formaldehyde. Two such commonly-used phenolics are p-phenylphenol/formaldehyde polymer and p-t-butylphenol/formaldehyde polymer. The former is expensive and now is seldom used. The methylene linkages in the latter subject the phenolic polymer to increased risk of formation of quinone methides. Because it is the formation of quinone methides that causes the polymer to darken, p-t-butylphenol/formaldehyde polymer tends to darken and therefore is not completely satisfactory.

Improvements in color and corrosion resistance can be made by substituting some bisphenol-A for p-t-butylphenol. It is generally accepted that the isopropylidene linkage in the bisphenol-A molecule decreases the tendency for quinone methide formation in phenolic polymers. Unfortunately bisphenol-A, because of the two hydroxyl groups, has very poor solubility with oils and the common solvents used in coating formulations. Therefore, only modest modifications with bisphenol-A can be used for these polymers.

Another class of phenolic aralkylation polymers also is useful in coating systems. Polyol polymers of this class exhibit improved oil solubility, improved compatibility with oil and alkyd-based polymers, as well as urethanes, epoxies and acrylates and a decreased tendency for color body formation and resultant darkening of coatings in which they are incorporated. The polymers can be made free of formaldehyde and phenol.

A lower melting polyol of this class is the phenolic aralkylation polymer reaction product obtained by aralkylating a phenolic monomer with at least one styrene derivative to obtain an aralkylated phenol, then reacting the aralkylated phenol with a coupling agent to obtain the phenol aralkylation polymer. Suitable coupling agents include aryl diolefins, formaldehyde, dialdehydes, and dibenzylic diols. The aralkylated phenol is joined to the coupling agent. Those skilled in the art will recognize the primary linkage is at the ortho position.

A higher melting point polyol of this class is a phenolic aralkylation polymer formed by reacting a phenolic monomer with an aryl diolefin to obtain a phenol/aryl diolefin polymer and then aralkylating the phenol/aryl diolefin polymer with at least one styrene derivative to obtain phenol aralkylation polymer, with a portion of the phenolic component joined to the aryl diolefin with a portion of the phenolic linkages being para in orientation.

The highly aromatic character of this class of polymers broadens the range of compatibility with other components of coating systems. Polymers of this class also exhibit enhanced physical properties, adhesion, and barrier properties. However, there exists a continuing need for high performance coating systems and components thereof.

SUMMARY OF THE INVENTION

The invention relates to polyol phenolic aralkylation polymers modified to improve the characteristics and properties of coating systems in which the modified materials are incorporated. In particular, the polymers are modified by esterification with fatty acids, transesterification with glyceride oils, or other modifications to reactive hydroxyl moieties. At least a portion of the hydroxyl moieties of the polyol is esterified or otherwise modified. The hydroxyl moieties include those that have been "chain-extended," if desired.

Control of the degree of modification can provide a desired balance of properties of the modified polymer and of the coating system comprising it. For example, retained hydroxyl functionality provides the ability to further react the modified polymer with di- and poly-isocyanates and with di- and poly-carboxylic acids. Modified polyols having a limited degree of retained hydroxyl functionality are satisfactorily grafted onto other coating polymer systems without gelation. Such a coating system is water-dispersible and air-drying. Incorporation of highly reactive fatty acid components achieves faster drying rates for air-drying coating systems.

DETAILED DESCRIPTION OF THE INVENTION

The invention is directed to polyol polymers modified by esterification with fatty acids, transesterification with glyceride oil, alkoxylation, other modification, or a combination thereof The modification of the polyols need not involve each hydroxyl moiety. Rather, the degree of modification affects the characteristics and properties of the modified polymer, and of a coating system comprising it, in a predictable matter. For example, modified polyols having a limited degree of retained carboxyl functionality provide a water-dispersible, air-drying coating system. Polyol esterified with highly reactive fatty acid components would be expected to provide an air-drying coating system having faster drying rates. Polyol modified by reaction with, e.g., glycerol acrylate carbonate, yields an acrylic-substituted molecule suitable for incorporation into acrylate polymers. These and other characteristics and properties of modified polyols, and of products comprising them, are set forth in additional detail below.

Throughout the remainder of this specification, the invention will be described in detail as it relates to the class of polyol polymers described above as "phenol aralkylation polymers." However, the invention also relates to other phenolics, including the p-phenylphenol, p-t-butylphenol, and bisphenol types described above, upon which modified phenolic polymers can be based. With the guidance provided herein, skilled practitioners will be able to apply the teachings of this document to not only select known compositions of matter but also to form modified products not described in detail herein.

The phenolic aralkylation polymers particularly useful in the practice of the invention are derived from a phenolic monomer, at least one styrene derivative, and a coupling agent. The coupling agent can be an aryl diolefin, formaldehyde, a dialdehyde, or a dibenzylic diol. Combinations of coupling agents also can be used. An aromatic coupling agent is preferred. Other moieties may be present to form a product having particular properties.

The phenol aralkylation polymers are produced by reacting these three components, preferably by a process having at least two reaction steps. In a preferred embodiment, the order of the reaction of the three reactants is arranged to provide a phenol aralkylation polymer product having desired properties. For instance, at least one styrene derivative is reacted with a phenolic monomer and then the product thereof is reacted with an aryl diolefin. Alternatively, a phenol monomer is reacted with an aryl diolefin, and then the product thereof is reacted with at least one styrene derivative. Similarly, a portion of either the styrene or aryl diolefin may be withheld for later reaction to achieve a predetermined polymer composition exhibiting a desired performance characteristic. The phenolic hydroxyl moieties then can be alkoxylated to provide at least one aliphatic hydroxyl moiety, if desired.

Reactants

Phenol monomers

The phenolic monomers include phenols which contain at least two free reactive positions. For example, in the case of phenol and substituted phenols, monomers contain at least two free reactive (ortho- or para- positions). Examples include phenol itself, o-, p- and m-cresol, m-isopropylphenol, 3,5-xylenol, 3,5-diisopropylphenol and mixtures of these compounds. Specific classes include:

I. Phenolic monomers containing mononuclear phenolic substituents as shown by the formula:

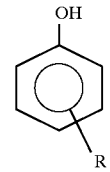

Substitution may be at the ortho, meta, or para positions. R may be methyl, ethyl, isopropyl, n-propyl, t-butyl, isobutyl, n-butyl, and aliphatic substituents having 5-10 carbon atoms. R also may be phenyl or a substituent derived from aralkylation with styrene derivatives, e.g styrene, p-methylstyrene, t-butylstyrene, mixed t-butylstyrenes, a-methylstyrene, and the vinyltoluenes, including the halo-substituted derivatives of each. R also may be derived from the reaction of a benzylic alcohol with phenol or a phenolic, benzyl alcohol, and the alkyl, alkylaromatic, aromatic, and halo derivatives thereof; i.e., methylol phenol, including the alkyl (up to about 10 carbon atoms) and aralkyl (up to about 12 carbon atoms) derivatives thereof; and methylol amide (such as methylol acryl amide), including the alkyl (up to about 10 carbon atoms) and aralkyl (up to about 12 carbon atoms) derivatives thereof. R also may be derived from a primary or secondary olefin having 2 to about 14 carbon atoms; an olefin (acrylic) acid or the ester thereof having up to about 14 carbon atoms; cyclopentene, cyclohexene, and the alkylaromatic derivatives of each; maleic anhydride and the ester, amide, and imide derivatives thereof; vinyltriazine; vinylacetate, and vinylformate.

II. Polyhydroxy mononuclear and polynuclear phenolic monomers include:

(1) Hydroquinone, resorcinol, and catechol

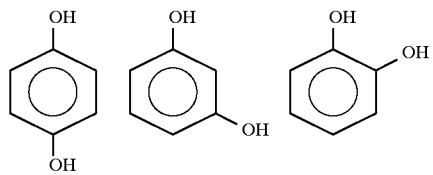

Hydrquinone    Resorcinol      Catechol (2)(a) Alkyl or aralkyl, mono- and di-substituted, hydroquinones

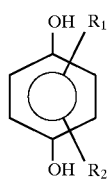

wherein the substitutions of $R_1$ and $R_2$ on the ring include 2,3; 2,5; and 2,6 positions; and $R_1$ and $R_2$, independently, can be hydrogen, alkyl having 1–10 carbon atoms, and aralkyl derived from styrenes, and benzylic derivatives, as previously described with regard to R. $R_1$ and $R_2$ can also be divinyl aromatics, which can give rise to chain extended systems, as taught herein, for monohydroxy phenolic monomers. The latter system advantageously requires minimal incorporation of the dihydroxy monomer into the polymeric product to achieve the desired high hydroxy, functionality.

(2)(b) Alkyl or aralkyl tri-substituted hydroquinones:

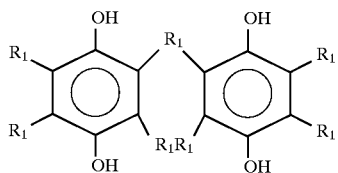

wherein the substitutions of $R_1$ on the ring independently can be hydrogen, alkyl having 1–10 carbon atoms, an aralkyl derived from styrenes, and benzylic derivatives, as previously described with regard to R. $R_1$ also can be a divinyl aromatic, which can give rise to chain extended systems, as taught herein, for monohydroxy phenolic monomers.

Incorporation of tri-substituted hydroquinone yields lower functionality polymers. Two or more such tri-substituted hydroquinones, or one such trisubstituted hydroquinone and a reactive polyhydroxyphenolic composition, such as resorcinol, also may be joined by a bridging group selected from the group consisting of formaldehyde, divinylaromatics, dibenzylicalcohols, other bridging groups described above, and blends thereof The latter provide higher functionality polymers.

(3) Alkyl or aralkyl, monosubstituted resorcinol

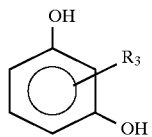

wherein $R_3$ is in the 2, 4, or 5 position on the ring. $R_3$ can be hydrogen, alkyl having 1–10 carbon atoms, aralkyl derived from styrenes, and benzylic derivatives, as previously described with regard to R. $R_3$ can be divinyl aromatic, which can give rise to chain extended systems, as taught for the monohydroxy phenolic monomers. Advantages of the latter systems include minimal incorporations of the subject monomer into an alkylation polymer to achieve the desired high hydroxy functionality.

Resorcinol substituted at the 5- position is of particular interest because the molecule retains 3 reactive positions (viz., the 2-, 4-, and 6- positions). Therefore, such molecules as 5-methylresorcinol can provide an additional substituent and still form a chain-extended polymer system.

Resorcinol can also be used in the disubstituted (alkyl or aralkyl) mode to produce lower functionality polymers and in combination with difunctionally reactive monomers such as hydroquinone or monosubstituted phenolics, as described herein.

(4)(a) Alkyl or aralkyl, mono- and di-substituted catechol

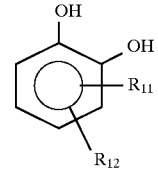

wherein the substitutions of $R_{11}$ and $R_{12}$ on the ring include the 3,4 or 3,5 positions and wherein $R_{11}$ and $R_{12}$ independently, can be hydrogen, alkyl having 1–10 carbon atoms, aralkyl derived from styrenes, or benzylic derivatives, as previously described with regard to R above. $R_{11}$ and $R_{12}$ can also be divinyl aromatics, which can give rise to chain-extended systems, as taught for the monohydroxy phenolics. The latter system also advantageously requires minimal incorporation of the dihydroxy monomer into the polymeric product to achieve the desired high hydroxy functionality.

(b) Trisubstituted catechol also can be used to produce lower functionality polymers, and in combination with difunctional reactive monomers, such as resorcinol or hydroquinone, as described above.

(5) Alkyl or aralkyl substituted polyhydroxy-polycyclic aromatic phenols. Examples include:
(a) Dihydroxynaphthalenes:
1,2-; 1,3-; 1,4-; 1,5-; 1,6-; 1,7-; 1,8-; 2,3-; 2,4-; 2,5-; 2,6-; 2,7-; particularly the 2,6- and 1,4- dihydroxynaphthalenes, and the alkylated and aralkylated derivatives thereof, as described above with regard to R.
(b) Dihydroxy derivatives of anthracene, phenanthrene, etc.

(6) Carboxylated hydroxynaphthalenes, carboxylated hydroxyanthracenes, and carboxylated phenanthrenes.

III. Polynuclear phenolic monomers include:
(1) Bisphenol A (p,p'-dihydroxydiphenyldimethylmethane).
(2) Bisphenol F (a mixture of the following three molecules)

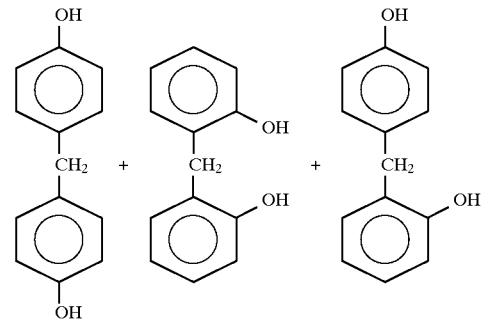

(3) Dihydroxy biphenyl-bisphenols derived from various means.
(a) Systems prepared by oxidatively coupling 2,6-disubstituted phenols, then partially or totally dealkylating the reduced coupled molecule.
(b) Disubstituted bisphenols derived from coupling of monosubstituted alkyl phenolics by action of the enzymatic coupling of phenols (Mead Process). The Mead Process is described in, for example, U.S. Pat. No. 4,900,671 which is hereby incorporated by reference.

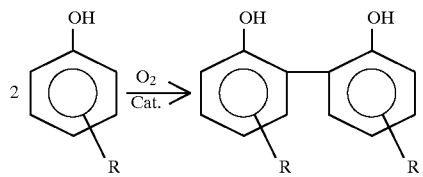

(4) Bisphenols or polymeric phenols coupled by
(a) an aldehyde or a ketone.

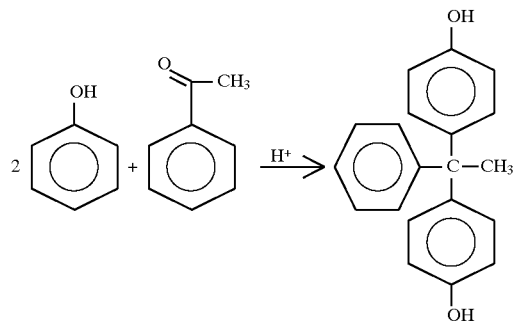

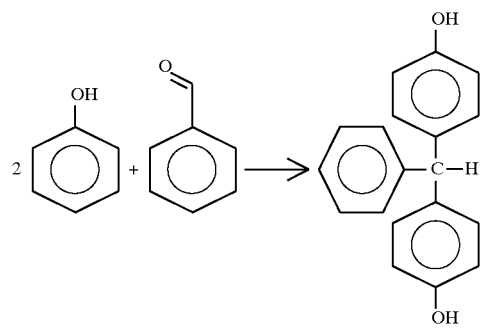

Particularly suitable aldehydes and ketones include acetaldehyde, benzaldehyde, hydroxybenzaldehyde, and acetophenone;

(b) Sulfone linkages generated from Friedel-Craft reaction of systems;

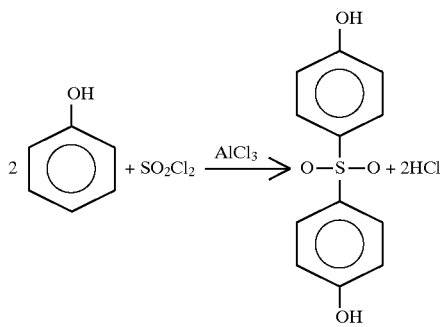

(c) Oxygen, sulfur, and phosphorus oxide derivatives (phosphate, phosphite, phosphonate, etc);

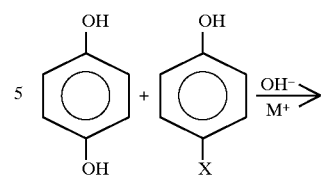

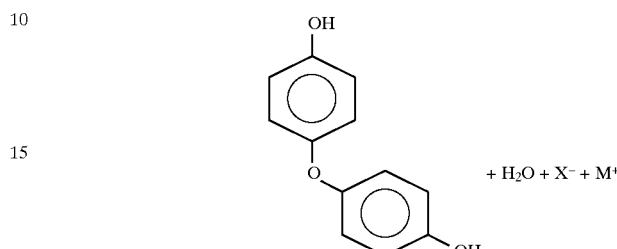

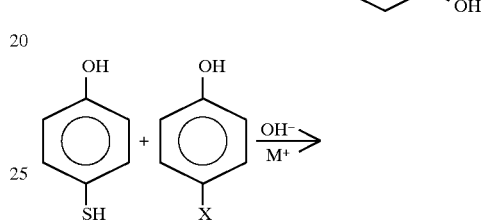

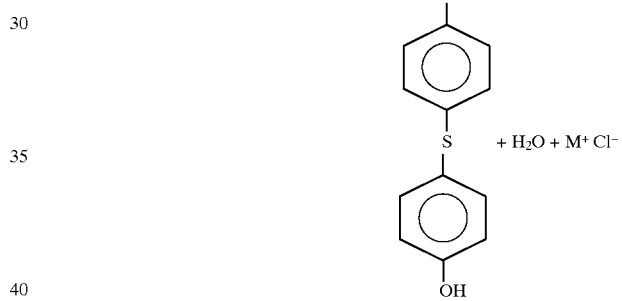

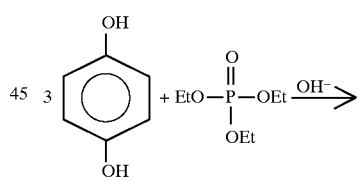

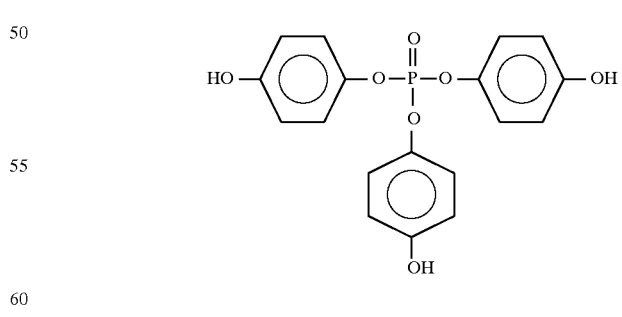

(d) Amines having up to about 20 carbon atoms;

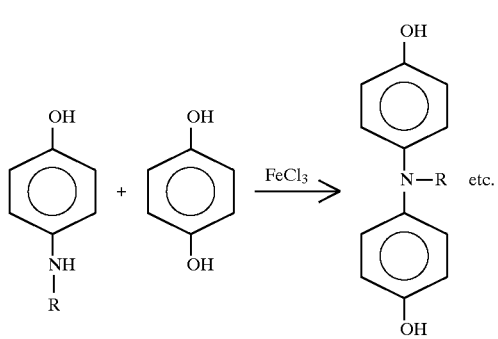

(e) Polyvinyl aliphatic compounds, especially butadiene, isoprene, cyclopentadiene, dimethylbutadiene, piperylene, dicyclopentadiene, limonene, other 5-carbon dienes, other 6-carbon dienes, and other cyclic dienes having between about 6 and about 9 carbon atoms;
(f) Aromatic diolefin compounds having at least one aromatic ring and 2 polymerizable carbon/carbon double bond moieties, particularly diisopropenylbenzene and the divinyl benzenes;
(g) Polybenzylic alcohols derived from xylenes and aldehydes, for example, formaldehyde;

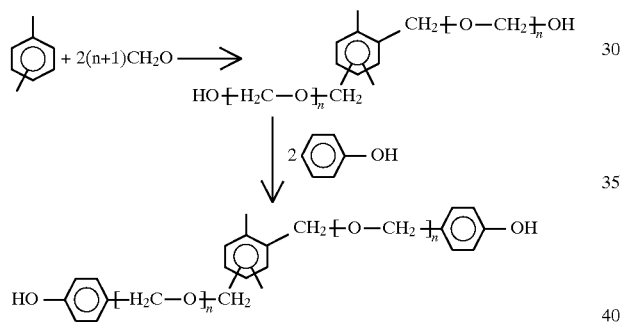

(h) Polybenzylicalcohols derived by oxidation of diethylbenzenes and diisopropylbenzenes;

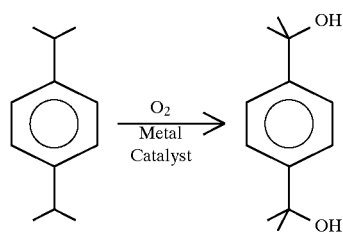

and
(i) Polyvinyl heterocyclic compounds, such as trivinyl triazine (acrylonitrile trimer); divinylmethyltriazine (obtained by trimerization of acrylonitrile/acetonitrile mixtures).
(5) Bisphenolics derived from diacrylic esters, diallylphthalate, bismaleimides, cyclohexanone, and isophorone, and their alkyl and aralkyl derivatives;
(6) Aromatic ester bisphenols such as those derived from the reaction of hydroquinone diacetate with 2 moles of p-hydroxybenzoic acid;

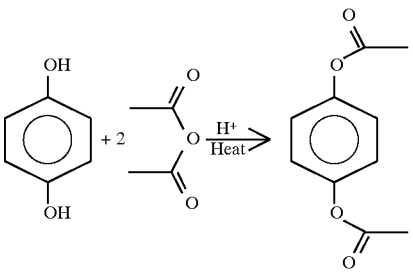

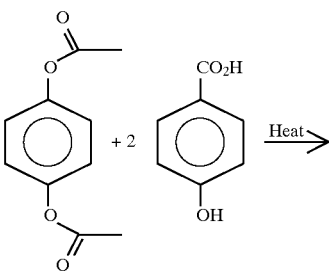

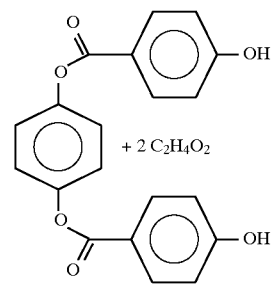

(7) Bisphenols prepared by the thermal or catalytic coupling of resoles.

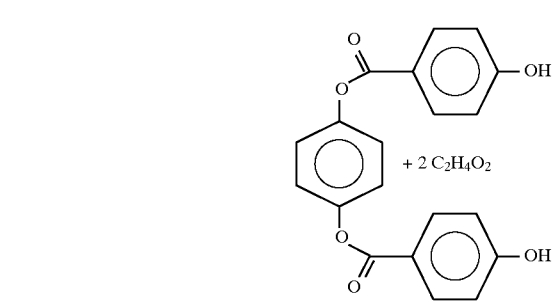

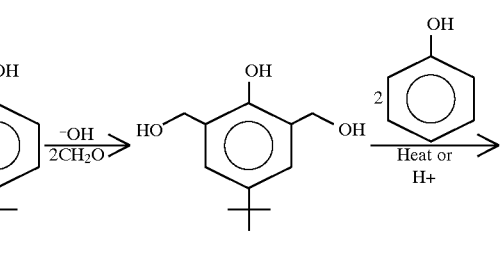

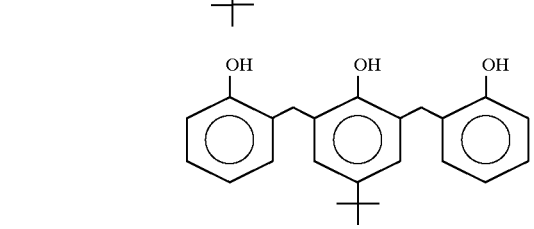

and (8) Bisphenol from a benzylic compound.

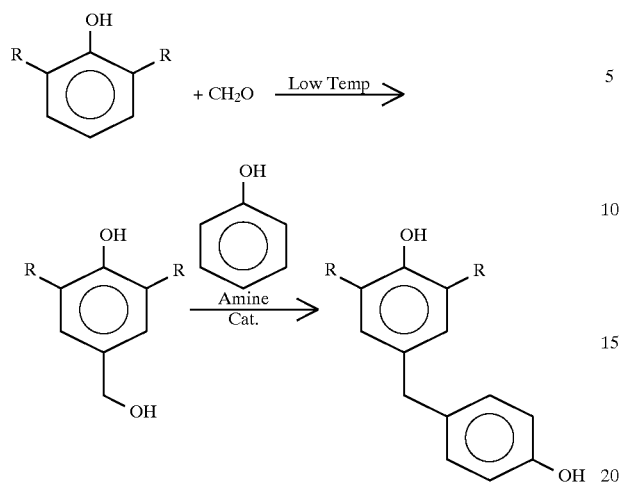

Preferred coupling agents are di- or poly-methyl systems derived from reaction of formaldehyde with phenol.

The phenolic monomers may be employed as an initial phenolic monomer in the reaction or may be employed as an additional phenolic monomer later in the reaction. Whether the phenolic monomer is used at an initial stage or as an additional component depends on the particular reaction scheme employed as discussed later. Preferred initial phenolic monomers are phenol, bisphenol A, bisphenol F, hydroquinone, resorcinol, 5-methylresorcinol, and catechol. Other preferred phenolic monomers include p-t-butylphenol, p-cumylphenol, and p-octylphenol which may be used as initial phenolic monomers or additional phenolic monomers depending on the particular reaction scheme employed. Polymers produced from the above monomers may also be used as the phenolic monomer.

Styrene Derivatives

The styrene derivatives may be any of the aryl substituted alkene hydrocarbons. Examples include styrene, α-methylstyrene, p-methylstyrene, p-t-butylstyrene, α-methyl-p-methylstyrene, β-methylstyrene, m-ethylstyrene, p-ethylstyrene, p-vinyltoluene, mixed vinyltoluenes, mixed t-butylstyrenes, mixed ethylstyrenes, mixed t-butylstyrenes with di-t-butylstyrenes, isopropenylnaphthalene, 2-methyl-1,1-diphenylpropene, 1-phenyl-1-pentene, and the like. Mixed styrene derivatives means a mixture of for example, p- and m- t-butylstyrenes. The preferred styrene derivatives are styrene and homologs of styrene of the formula

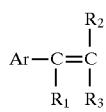

where Ar may be phenyl, naphthyl, biphenyl, or substituted phenyl, naphthyl, or biphenyl. In the later case, examples of substitutions may be:

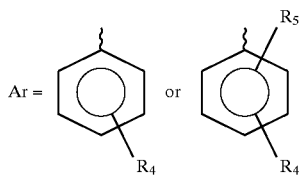

where R4 and R$_5$ are independently methyl, ethyl, C$_3$ to C$_{10}$ alkyl, or a halogen. R$_1$, R$_2$ and R$_3$ are independently hydrogen, an alkyl radical containing 1 to 5 carbon atoms, an aromatic or an alkyl aromatic. R$_1$, R$_2$ and R$_3$ can be other functionalities such as a carboxyl, as in the case of cinnamic acid.

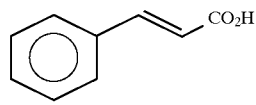

Such systems are particularly valuable as a means of introducing carboxyl functionality, as follows:

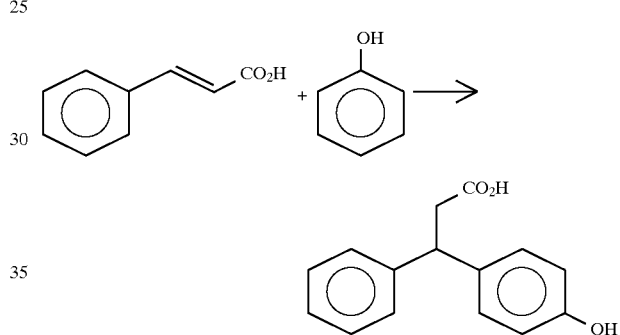

R$_1$, R$_2$ and R$_3$ can be alkoxy (—O—R') groups. Esters of styrene derivatives may also be used.

Preferably, the styrene derivative is styrene, α-methylstyrene, p-t-butylstyrene, m-ethylstyrene, p-ethylstyrene, p-vinyltoluene, mixed vinyltoluenes, mixed t-butylstyrenes, mixed ethylstyrenes, mixed t-butylstyrenes with di-t-butylstyrenes, or mixtures thereof Coupling Agents The preferred aryl diolefin coupling agent can be represented by the following formula:

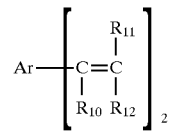

wherein Ar is benzene, naphthalene, or biphenyl; R$_{10}$, R$_{11}$ and R$_{12}$ independently are a hydrogen or an alkyl radical containing 1–5 carbon atoms. The orientation on the benzene ring is meta or para or mixtures thereof.

Possible substitutions for naphthalene include 1–3, 1–4, 1–5, 1–6, 1–7, 1–8, 2–4, 2–5, 2–6, 2–7, or 2–8 positions, and corresponding mixtures thereof.

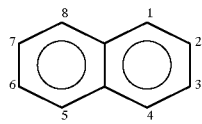

Possible substitutions for biphenyl include 1–3, 1–2', 1–1', 1–3', 2–3', and 3–3' positions, and corresponding mixtures thereof.

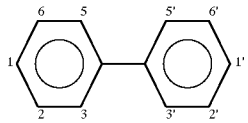

The aromatic nucleus may be substituted with various R groups, for example, methyl and t-butyl.

Preferably the aryl diolefin is m- or p-diisopropenylbenzene (DIPB) or their in, p mixtures or mixed m/p divinylbenzene (DVB) of any of the commercially available concentrations. m-DIPB is commercially available at a 98 percent concentration. DVB is available at concentrations of, for example, 53 percent, 62 percent, and 80 percent. Commercial sources of DVB also contain ethylstyrene (vinylethylbenzene). For instance, 80 percent DVB contains approximately 20 percent ethylstyrene. Diols derived from DIPB such as m or p diols of diisopropylbenzene are acceptable diolefin materials. Diols derived from hydration of DIPB such as m or p diols of diisopropylbenzene are acceptable precursor materials for aryl diolefins since they can be considered blocked aryl diolefins.

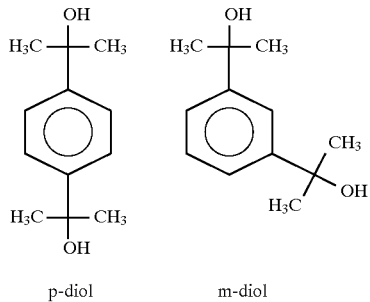

All or a portion of the styrene derivatives or aryl diolefin may be produced in situ by dehydration of methylbenzylic alcohols at reaction temperatures above 100° C. and acidities sufficient to promote dehydration of the benzylic alcohols. The resulting styrene derivative or aryl diolefin may be reacted with a phenolic monomer. Other means to produce the reactants in situ that are within the skill of the art are within the scope of the present invention.

Skilled practitioners recognize that cumyl alcohol and x-methylstyrene both generate the same benzylic carbonium ion which is the recognized intermediate required for generation of the subject styrenated or divinylarylated phenolic polymers. It will be noted that use of the DIPB diols requires their incremental addition to a phenolic containing reaction mixture under conditions allowing the simultaneous removal of the water produced from removal of the blocking group.

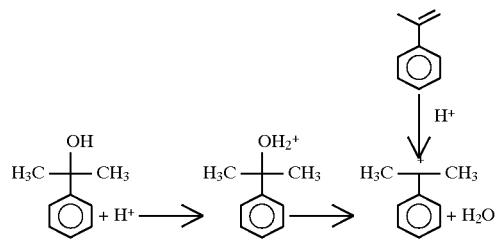

Resin thus produced has low monomer content (<1 percent) and excellent yields without the use of another coupling agent, such as formaldehyde. However, in either of the reaction schemes identified above, another coupling agent may be substituted for all or part of the aryl diolefin. Another coupling agent may be added at any stage of the reaction to increase phenol monomer linking. Suitable coupling agents include the following:

(1) Formaldehyde, including formaldehyde derived from, e.g., paraformaldehyde, hexamethylenetetramine, trioxane, and formaldehyde trisulfite.

(2) Any of the coupling agents identified above with regard to formation of bis- and poly-phenols.

(3) γ-Hydroxybutyraldehyde.

(4) Dichlorinated alkylenes, especially methylene chloride and ethylene dichloride.

(5) (a) Dibenzylic halides, alcohols, and methyl ethers, each derived from the xylenes, the ethylbenzenes, and isopropylbenzenes through substitution reactions or derived from divinyl or diisopropenylbenzenes by addition or solvolysis reactions.

(b) Dibenzylic alcohols derived from phenolics, as illustrated in the following formula:

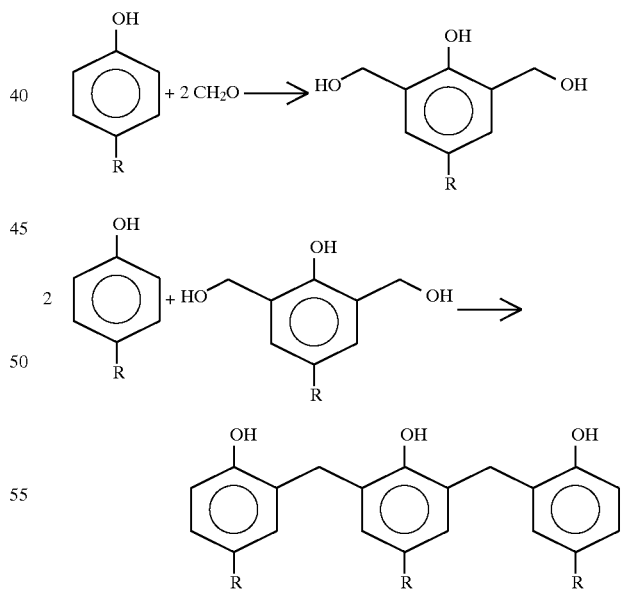

wherein each R is separately alkyl, aralkyl, and blends thereof.

(6) Glyoxal and glyoxalic acid.

(7) Dimethylol compounds derived by formaldehyde addition to phenol, "active hydrogen compounds," i.e., hydrogen moieties next to or in proximity to strong electron-withdrawing groups, as illustrated below in formula 1, such as acetone alcohol, nitroalkanes methylolated with formaldehyde and the "reduced" amine forms of these methylolated nitroalkanes, as illustrated in formula 2, acetophenone, and the like.

Active Hydrogen Compounds

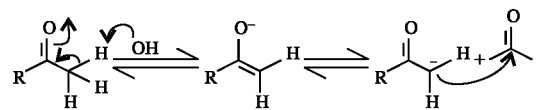

{The carbanion is stabilized by the oxygen.}

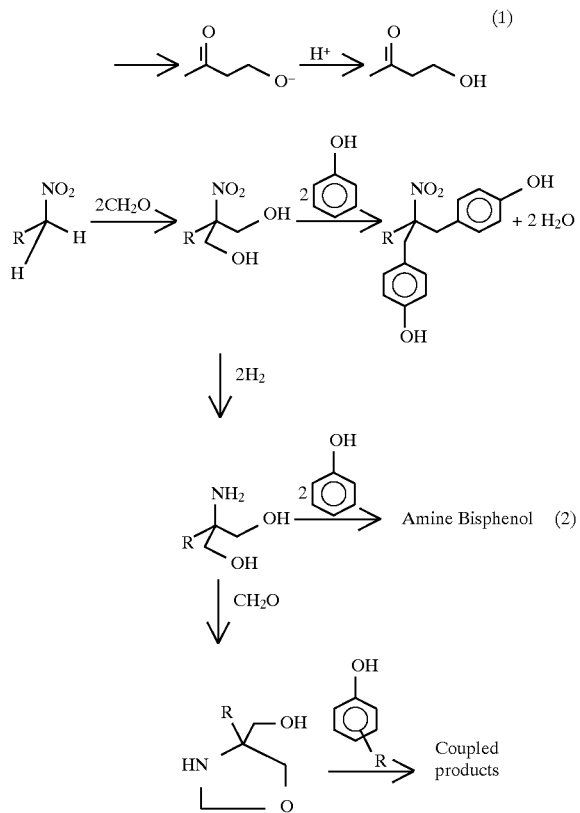

(8) Mannich bases derived from diamines and aldehydes or ketones, as follows:

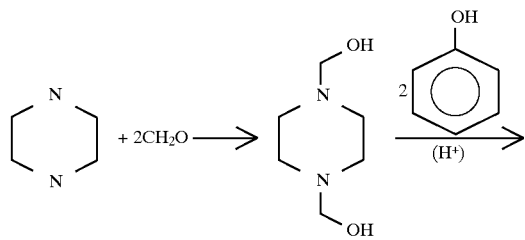

-continued

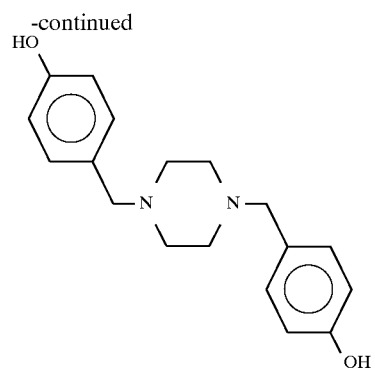

(9) Polyhalo or polymethylol compounds to give higher coupled analogs. Skilled practitioners recognize that an acidic or Lewis acid environment during reaction is appropriate when formaldehyde or the dihalide compounds are used as coupling agent.

The coupling agent is used at a range of mole ratios relative to the phenolic component. The mole ratio of coupling agent to phenolic component may be from 0.2:1 to 1.1:1. The mole ratio>1 is used under circumstances in which alkyl or aralkyl substituted phenolics are used and in which high molecular weight product is desired. The lower end of the mole ratio range is employed under circumstances where a low level of chain extension is required. The amount of coupling agent also depends on the amount of phenolic hydroxy substitution on the phenolic pre-polymer or monomer used. In the case of bisphenol A (a di-functional phenolic monomer), less coupling agent may be required to give a desired degree of phenolic functionality in the resultant polymer, because the monomer is higher in both molecular weight and functionality to start with. Similarly, a formaldehyde-linked phenolic polymer can be further coupled with coupling agents to build molecular weight to desired levels. The converse is also true that an aralkylation polymer formed from phenolic and coupling agent components can be further increased in molecular weight by reaction with formaldehyde under the conditions used to prepare the aralkylation system. A preferred range of mole ratio is 0.4:1 to 0.8:1.

The degree of styrenation employed with this polymer class can also vary. For the purposes of this invention, the degree of styrenation is defined as the ratio between the moles of styrene derivatives used and the molar equivalent of open reactive positions per phenolic monomeric component. The degree of styrenation is determined by subtracting the number of reactive positions used to couple with the aryl diolefin or other linking group from the total number of reactive positions per monomer. For example, phenol is considered to have 3 reactive positions. If two phenol molecules are coupled with an aryl diolefin, two open positions remain per phenol ring. The theoretical mole ratio for styrenation (moles of styrene per phenol molecule) is therefore 2. For the present invention, the effective range for styrenation is from 20 to 100 percent of the theoretical mole ratio, preferably 30 to 99 percent of theoretical, with the most effective range being 40 to 95 percent of theoretical.

Alkoxylating Agents

The phenolic aralkylation polymers can be further reacted with an alkoxylating agent selected from the group consisting of alkylene oxides and alkylene carbonates to provide at least one aliphatic hydroxyl moiety.

Alkylene oxides contain an epoxide group. Suitable alkylene oxides are epoxides in which one or both of the epoxide carbons is substituted with hydrogen or a $C_1$–$C_{10}$ alkyl, aryl, or aralkyl group. Preferred alkylene oxides are $C_2$–$C_4$ epoxides, including ethylene oxide, propylene oxide, isobutylene oxide, 1,2-butylene oxide, and 2,3-butylene oxide. Alkylene oxides that contain halogenated alkyl groups, such as epihalohydrins, also can be used. Propylene oxide, ethylene oxide, and isobutylene oxide are particularly preferred.

Alkylene carbonates are cyclic carbonates that contain —O—$CO_2$— in a five-membered ring. Suitable alkylene carbonates are cyclic carbonates in which one or both of the aliphatic ring carbons is substituted with hydrogen or a $C_1$–$C_{10}$ alkyl, aryl, or aralkyl group. Preferred alkylene carbonates are ethylene carbonate, propylene carbonate, and butylene carbonates.

As the result of alkoxylation, the aliphatic hydroxyl moiety is formed by opening of the oxirane or carbonate ring of the alkoxylating agent by the phenolic hydroxyl moiety. Other alkoxylating agents can be employed to provide other functional groups. For example, reaction of a phenolic hydroxyl moiety with butadiene oxide provides a pendant substituent having both hydroxyl and vinyl moieties, as follows:

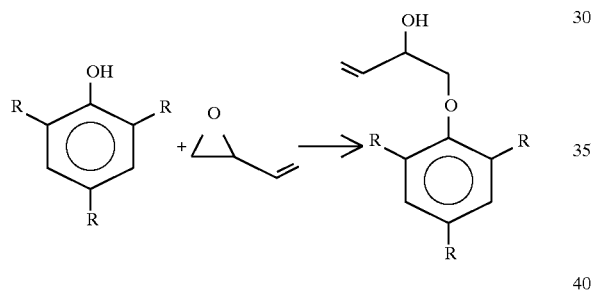

wherein R is as defined herein for this type of composition. The presence of two potentially reactive moieties increases the range of reactivity possible for thus-formed phenolic polymers and allows incorporation of the alkoxylated substituent into free radical polymerization while retaining the ability to engage in phenolic aralkylation reactions.

Similarly, butadiene carbonate can be reacted with a phenolic hydroxyl moiety without the production of undesirable chain-extending byproduct. As with the reaction of butadiene oxide, dual olefin/hydroxyl functionality results, as shown in the following formula:

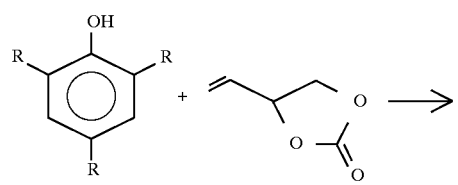

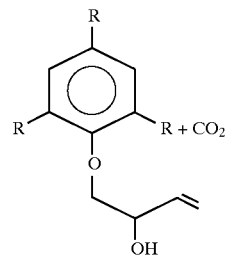

wherein R is as defined herein for this type of composition.

Two vicinal aliphatic hydroxyl functionalities can be introduced by alkoxylation of a phenolic hydroxyl moiety with glycerol carbonate, in accordance with the following reaction:

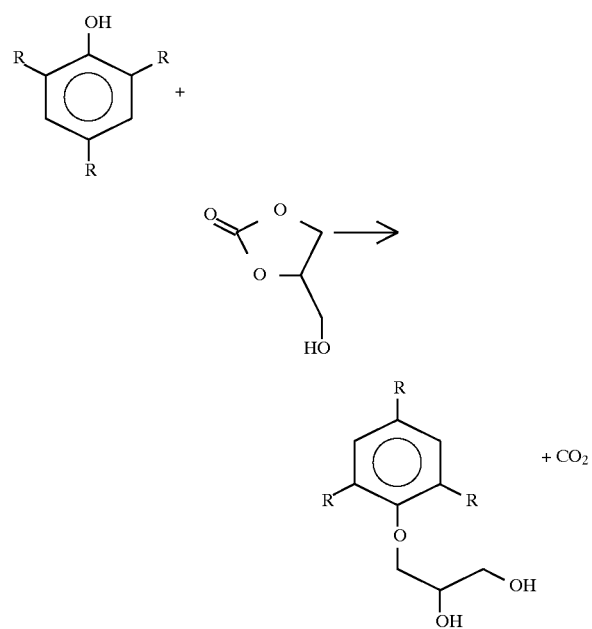

wherein R is as defined herein for this type of composition. The resultant product is valuable in the preparation of "hyperbranched" esters of fatty acids and other reactive functionalities to give highly cross-linked systems, and is particularly useful in uralkyd applications. The vicinal diols can also be trans-esterified with ethylene carbonate to generate carbonate-substituted aralkylation phenolic compositions suitable for crosslinking with polyamines at low temperatures.

Acrylate esters of glycerol carbonate are useful as intermediates by which acrylate functionality can be introduced to polymers of this invention, as follows:

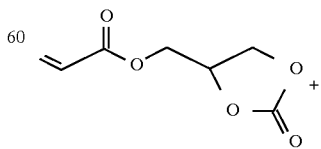

-continued

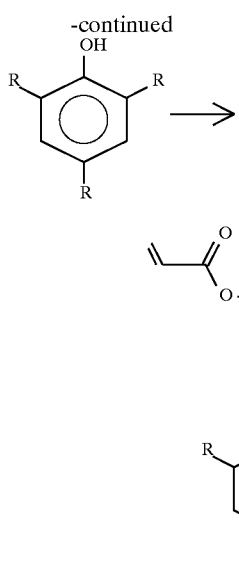

wherein R is as defined herein for this type of composition.

Glycidyl (meth)acrylate can be reacted with a phenolic hydroxyl moiety in the presence of a basic or Lewis acid catalyst to provide an alkoxylated acrylate useful for generation of free radical thermoset polymer systems, as follows:

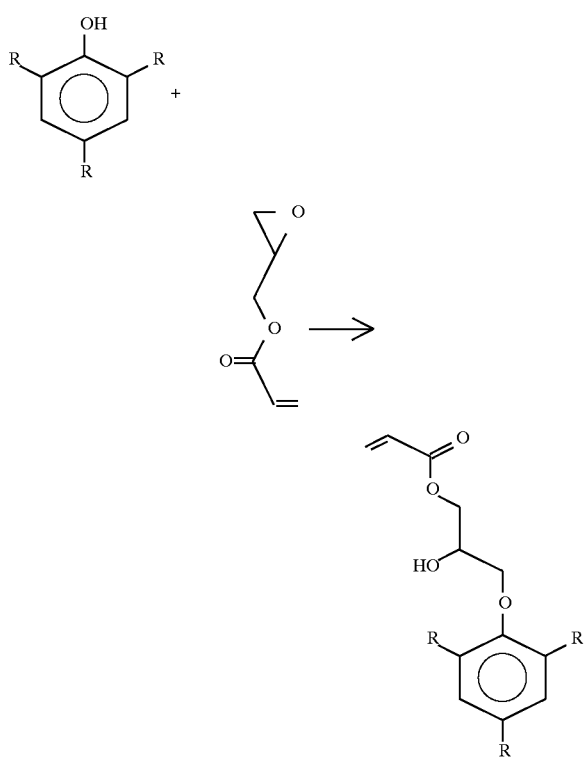

wherein R is as defined herein for this type of composition.

Lactones, including but not limited to butyrolactone and caprolactone, react with the phenolic hydroxyl moiety to produce monomeric or chain-extended aromatic polyester, in accordance with the following reaction:

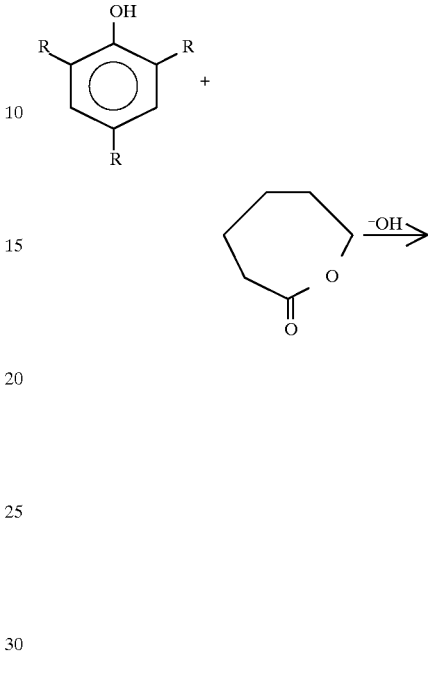

wherein R is as defined herein for this type of composition.

These resulting polyesters can be further acrylated or modified with TOFA to generate useful coating additives.

Diepoxies and higher additives of difunctional aralkylation polymers also are contemplated in accordance with this invention. Such products are generated from dihydroxyfunctional aralkylation products and difunctional epoxides. Suitable diepoxies include diglycidyl derivatives of bisphenol A and chain-extended derivatives thereof, aliphatic diepoxides based on the action of peracetic acid on cyclodiolefins, ester-linked cyclic diolefins, and diglycidyl ethers of diols and of other diols formed by alkoxylation of diols.

It has been discovered that epoxies can be rendered soluble in and compatible with non-polar solvents and polymers. Two types of products can be made in accordance with the invention. A "star" polymer can be made by reaction of the epoxide with a phenolic aralkylation polymer having a functionality of at least 2. A linear polymer can be made by reaction of the epoxide with a difunctional phenolic polymer. The following formula is representative of the latter:

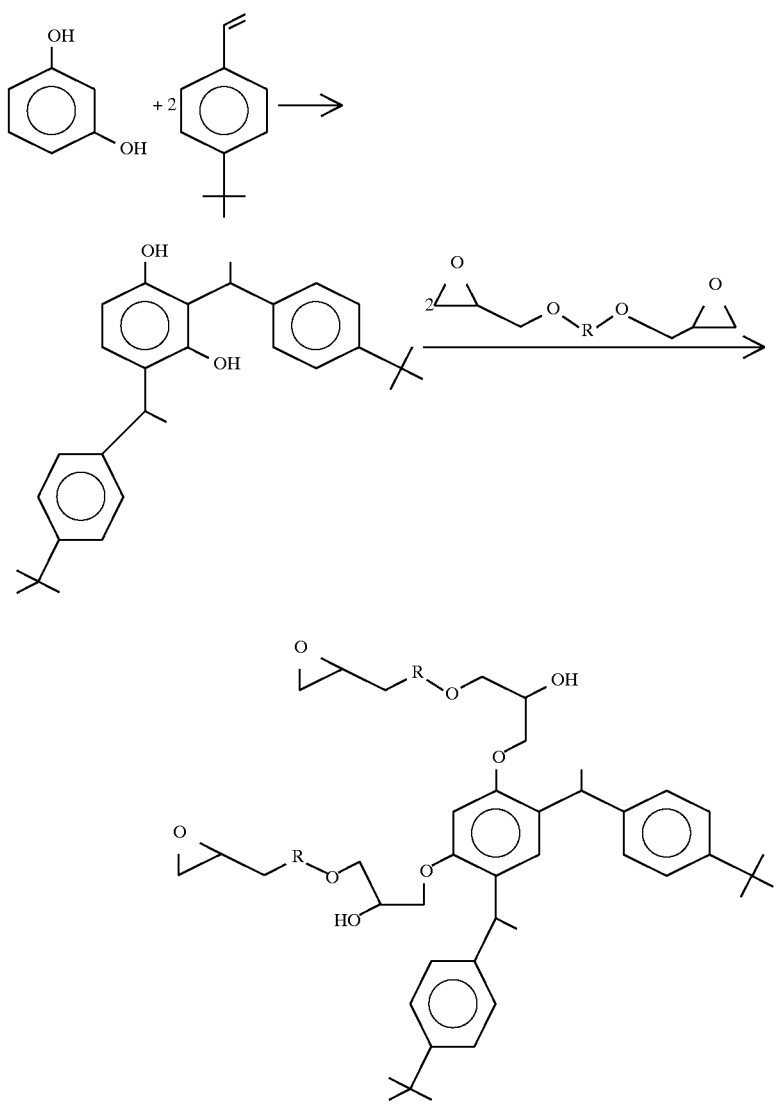

Linear polymers of this type in solid form are powder coating components.

Process

One way of forming a phenol aralkylation polymer is by aralkylating a phenolic monomer with at least one styrene derivative to obtain an aralkylated phenol, then reacting the aralkylated phenol with a coupling agent to obtain the phenol aralkylation polymer, with the aralkylated phenol joined together by the coupling agent. Those skilled in the art will recognize the primary linkage is predominantly at the ortho position. The resulting polymer then can be alkoxylated.

In accordance with this embodiment, a phenolic monomer and at least one styrene derivative are reacted in the presence of an acid catalyst. The pH of the reaction mixture is lowered by means of acid catalyst addition. Since the system is generally low in water content, the effective acidity of the catalyst system is increased.

Acid catalysts which may be used in preferred practice include but are not limited to:

- Alkylsulfonic acids - methane, ethane, and higher alkyl $C_3$–$C_{10}$;
- Arylsulfonic acids, toluene, xylene, and mixtures thereof; also, naphthalene sulfonic and aralkylated toluene, benzene, or naphthalene sulfonic acids containing $C_1$–$C_{10}$ alkyl substituents;
- Phenol sulfonic and sulfonated phenolic polymers which may include aralkylated phenolics;
- Sulfuric acid;
- Phosphoric acid;
- Alkyl, aryl or aralkyl phosphate esters having at least one free acidic proton per molecule;
- Phosphate esters, such as triethanolamine triphosphate, derived from hydroxyamines such as triethanolamine:

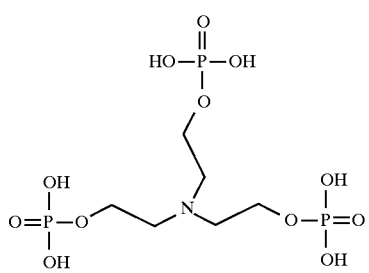

Hydrochloric acid;

Latent acid catalyst systems including organic acid chlorides, phosphorous oxychlorides, and the like;

Latent catalysts derived from alkyl esters of strong acids;

Latent acid catalysts derived from amines and the above;

Oxalic acid, maleic acid and other strong organic diacids having initial pKa's <1.5;

Halogenated organic acids such as chloroacetic and trifluoroacetic acid; and

Lewis acid catalysts based on halides of the Group III elements, particularly the chlorides and fluorides thereof are useful in combination with other catalysts described above. Complexed versions of catalysts of this class also are useful. The complex of a suitable Lewis acid catalyst with an alkyl aromatic composition, such as toluene or xylene, is a more selective catalyst than the equivalent uncomplexed version thereof Similarly, latent versions of the above-described Lewis acids are useful at elevated temperature to give selective catalysis. Fluorohaloborates of organic compounds also are examples of suitable catalyst, with stable carbonium ion-containing compounds being most desirable. The following formula, in which X is Cl, Br, F, or I, illustrates the preparation of such a catalyst:

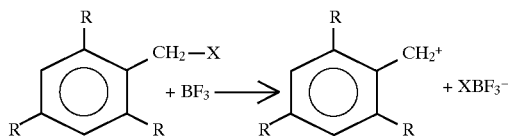

wherein X=Cl, Br, F, I.

Other weaker Lewis acids also are useful as catalysts for selective reactions. The titanium alkoxides, which are useful as transesterification catalyst, also can be used at elevated temperature to catalyze aralkylation with certain activated olefins, preferably a styrene derivative, which then are hydrated to provide alcohol moieties.

Neutral or basic catalyst can be used to affect aralkylation of phenolic compounds. These catalyst systems are well known as ortho alkylation catalysts. These catalysts are suited to affect reaction between a phenolic molecule having at least one ortho-reactive position and an activated olefin, such as styrene or its derivatives, and diolefinic compounds.

These catalysts may be any of the materials known to catalyze the ring alkylation of hydroxybenzene in the ortho position. Such materials include metal phenate derivatives of Al, Mg, Fe, Zn, P, As, Sb, Bi, and Sn; the polymeric or supported aluminum alcoholates of the type set forth in U.S. Pat. No. 3,733,365; and the aluminum mixed salts described in U.S. Pat. No. 3,267,154; both patents are incorporated herein by reference. The alkoxy derivatives of Zr, Hf. Nb, and Ta also are suitable catalysts. Aluminum is a preferred catalytic component. The aluminum alkoxide intermediates are believed to be analogues to those postulated in other reductive processes, illustrated as follows:

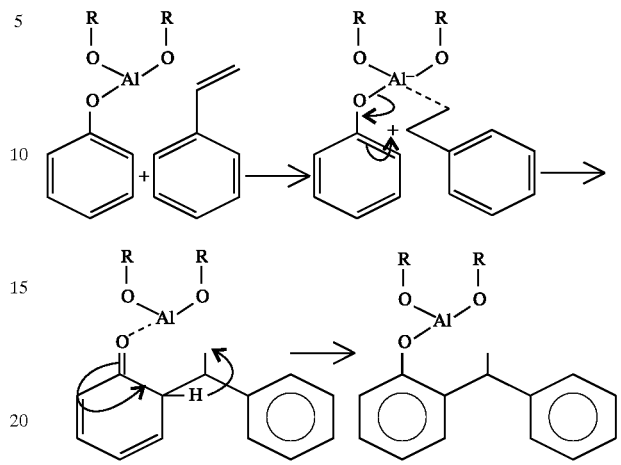

wherein R is an aromatic moiety of the phenolate ion.

Reactions of the type described above are useful in aralkylation of materials such as bisphenol-A without the undesirable retro-reaction of the isopropylidene coupling linkage that typically occurs in the acid catalyzed alkylation reaction.

The amount of acid catalyst required depends on the effective acidity and type of catalyst selected. Strong acids such as sulfonic and methane sulfonic require quantities less than 0.20 percent based on the total reactive charge providing that said reactants do not contain basic impurities which would neutralize the catalyst. It will be noted that dilute solutions of said acids can be used provided that provisions are made to remove water from the reaction mixture. Weaker acids require the use of a larger quantity, skilled practitioners are familiar with methods for optimization thereof. The ortho orientation catalysts require an effective amount of catalyst, typically from about 0.001 mole of catalyst per mole of olefin hydrocarbon, up to about 0.1 mole of catalyst per mole of olefinic hydrocarbon.

The temperature of the reaction depends on a number of factors and is preferably between 120–160° C. The temperature selected depends on the nature of the aralkylating agent and requires optimization for each system. In some instances, higher temperatures are desired to insure against O-aralkylation of the phenolics in accordance with the following reaction:

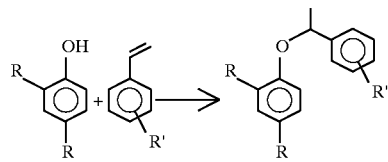

whereas, in other instances, lower temperatures are desirable to minimize retro-aralkenylation with the resultant formation of undesired aryl olefin-coupling homo-polymeric products. In any case, the reaction time required can vary significantly, but the reaction is generally considered complete in the 10–30 minute time frame at the average (140° C.) reaction temperature. This combination of conditions can be applied to all combinations of phenol, substituted phenols, and phenol aralkylation products with either styrene, its derivatives, or coupling agents. It is worth noting that the aralkylation reaction is stopped completely by neutralization of the acid catalyst, and that systems so stabilized can be heated to temperatures in the 200–250° C. range for substantial periods without rearrangement, dealkylation, or other similar decompositions.

The phenolic monomer is selected to provide an aralkylated phenol and is preferably selected from phenol, bisphenol A, bisphenol F, hydroquinone, catechol, or resorcinol. Additional phenolic monomers may be added prior to reacting the aralkylated phenol with the aryl diolefin such as p-t-butylphenol, p-cumylphenol and p-octylphenol. It is within the skill of the art to determine what phenolic monomers are appropriate to react with the styrene derivative to obtain an aralkylated phenol and what phenolic monomers may be added later to build the polymer.

The ability of the phenolic monomer to form an aralkylated derivative by reaction with benzylic alcohol is an important characteristic of the phenolic monomer. The resultant derivatives are analogous to the vinyl and isopropenyl aromatics described herein. It has been discovered that readily available 2,6-dialkyl phenolic compositions are readily methylolated at the para positions to provide alkylated aromatic derivatives which impart the desired hydrocarbon solubility to the polymers of this invention. The following reactions are illustrative.

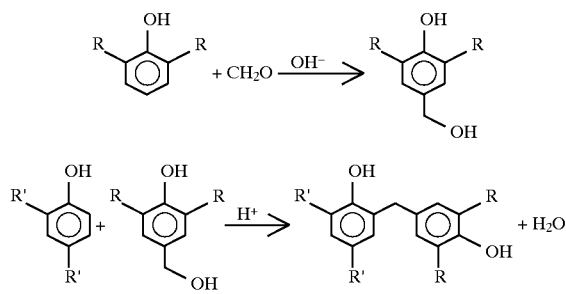

wherein each R and R'is as defined herein for these types of compositions.

The aralkylated phenol product is then reacted with a coupling agent to obtain the phenol aralkylation polymer, with the aralkylated phenol joined to the coupling agent primarily at the opposition. The pH of the reaction mixture is lowered by means of acid catalyst addition. If the coupling agent is a diolefin, the same catalysts can be considered for the diolefin reaction with the styrenated phenols as were used to promote the reaction of phenol or its derivatives with aryl olefins. Indeed, in practice of this invention, the same catalyst system is normally used to conduct the divinyl aromatic-phenolic polymerization reaction as was used for the precursor phenolic reactant styrenation.

Acid catalysis can be used when an aldehyde, such as formaldehyde or glyoxyaldehyde, is used as coupling agent. A preferred embodiment of the invention is to conduct the reaction with formaldehyde as a "capping" reaction, i.e., the reaction mixture is heated to about 110° to 120° C. with about 20–25 wt percent o-xylene in the reactor, with the aralkylated phenolic material making up the remainder of the reactor charge. The aldehyde reactant, typically 50 wt percent formaldehyde solution, is added incrementally over a period of about 1 hour. The aldehyde reacts quickly at the acid catalyst concentration used to effect the initial aralkylation reaction. The formaldehyde solvent water is removed by azeotropic distillation with the o-xylene. The distillate is collected in a decanter, from which the water can be removed to recover the solvent. The efficiency of aldehyde usage is greater than about 95 wt percent.

After completion of the aralkylation reaction, the final product is neutralized and made sufficiently basic to allow the desired degree of alkoxylation. Generally, a 50 wt percent aqueous solution of alkali metal oxide or hydroxide is used to neutralize the product. Potassium hydroxide is a preferred neutralizing agent.

Another method of forming a phenol aralkylation polymer is to first react a phenolic monomer with a coupling agent to obtain a coupled phenol polymer and then to aralkylate the coupled phenol polymer with at least one styrene derivative to obtain the phenol aralkylation polymer, with the phenol joined, as those skilled in the art will recognize, to the coupling agent primarily at the ortho and para positions.

In accordance with this embodiment, a phenol and a coupling agent are reacted to form a coupled phenol polymer. The pH of this reaction mixture is lowered by means of acid catalyst additions. The same catalyst systems and processing conditions are required for these embodiments as were described earlier for aralkylation of the unsubstituted phenolic systems using styrene or substituted styrenes.

The coupled phenol polymer is then aralkylated with a styrene derivative in the presence of an acid catalyst to obtain the phenol aralkylation polymer. The same acid catalysts can be considered for styrene aralkylation of the above phenol aralkylation polymer as were used to react the aryldiolefin with the phenolic reactant. Indeed, in practice of this invention, the same catalyst is used to catalyze both the styrene and diolefin reactions with phenol and its derivatives. The final product can be neutralized with caustic, potassium hydroxide, or an organic base such as guanidine carbonate. Any of these catalysts is capable of promoting the alkoxylation reactions, as described below. Potassium hydroxide is a preferred inorganic catalyst; guanidine carbonate is particularly advantageous when it is preferred to minimize salt contamination of the product.

Polymers produced by initially reacting a phenol with an aryl diolefin generally result in higher melting point polymers than those produced by reaction of the aryl diolefin with preformed para styrenated phenolics.

In another embodiment of the present invention, the phenolic monomer is reacted with a portion of the coupling agent, and then with the remaining coupling agent after aralkylation of the phenol with the styrene derivative. Polymers produced in this manner have advantages such as minimizing the potential for gel formation.

Alkoxylation generally requires an alkoxylation catalyst. Catalyst can be omitted, but reaction times are longer, and higher temperatures are needed. Generally, the phenolic aralkylation polymer is heated with the alkylene carbonate or alkylene oxide in the presence of the alkoxylation catalyst under conditions effective to produce the desired reaction.

Suitable alkoxylation catalysts include alkali metals; alkali metal and alkaline earth metal alkoxides, hydroxides, hydrides, carbonates, bicarbonates, oxides, sulfonates, amides, acetonylacetates, carboxylates, and phenolates; tertiary amines; alkylammonium halides, hydroxides, alkoxides, bicarbonates, and carbonates; Lewis acids (e.g., boron trifluoride, aluminum chloride, tin tetrachloride); inorganic acids (e.g., HCl, $H_2SO_4$); carboxylic acids; sulfonic acids; metalloporphrins; dialkylzinc compounds; and double metal cyanide compounds. Other catalysts useful for alkoxylation appear in K. J. Ivin and T. Saegusa, *Ring-Opening Polymerization*, Vol. 1 (Elsevier) 1984, Chapter 4, "Cyclic Ethers." Additional examples are found in U.S. Pat. Nos. 3,393,243, 4,595,743, and 5,106,874, the teachings of which are incorporated herein by reference.

Potassium hydroxide is preferred catalyst when standard alkali metal catalysis is preferred. It is advantageous to use the known ease with which potassium ion forms alkoxide, then use the potassium ion to catalyze reaction between propylene oxide and the aliphatic hydroxyl moieties. Although the inventors do not wish to be bound by theory, it is believed that the reaction-initiating agent is phenoxide anion formed by the reaction of a phenolic hydroxyl moiety with the basic potassium salt. It is further believed that chain extension of the alkoxyl moieties occurs only after the phenolic hydroxyl moieties and water have reacted with the propylene oxide. Thus, when propylene oxide is employed as the alkoxylating agent, the system preferably is made nearly anhydrous.

In contradistinction, the alkylene carbonates generate $CO_2$ as a byproduct of the alkoxylation reaction, thus preventing the reaction mixture from attaining a pH which is sufficiently high to generate the alkoxide anion required to achieve alkoxylene chain extension. Thus, reaction of an alkylene carbonate with a phenolic hydroxyl moiety produces only monoalkoxylation products. The inventors have discovered that guanidine carbonate is suitable as an alkoxylation catalyst. Skilled practitioners recognize that guanidine is the strongest neutral organic base. Indeed, guanidine has a basicity comparable to that of the alkali metal oxides and alkoxides. Thus, guanidine carbonate can be added to a phenolic alkylation polymer formed by acid catalysis to neutralize the product. At slight excess of guanidine carbonate, a sufficiently high pH is achieved to readily catalyze the reaction between alkylene oxides, alkylene carbonates, diene oxides, diene carbonates, glycerol carbonate, glycerol carbonate (meth)acrylate, glydicyl (meth)acrylate, and lactones; preferably ethylene oxide, ethylene carbonate, propylene oxide, propylene carbonate; and the hydroxyl moieties of a phenolic aralkylation polymer. Such catalysis has at least three significant advantages, as follows:

(1) the susceptibility to formation of oxidatively induced color bodies is reduced;

(2) methane sulfonic acid salts of guanidine and its products remain soluble in most alkoxylation products, thus eliminating the need for expensive salt removal; and (3) guanidine byproducts appear to form products compatible with TOFA used in many applications of alkyd coating technology.

The amount of catalyst needed in any case depends on the type of catalyst used, the particular catalyst chosen, the reaction conditions used, the nature of the phenolic aralkylation polymer, and other factors. Generally, the amount of catalyst needed will be within the range of about 1 ppm to about 5 wt. percent based on the amount of phenolic aralkylation polymer. Those skilled in the art will understand how to adjust the amount of catalyst used based on these factors to permit an efficient synthesis of the phenolic aralkylation polymers.

The relative amounts of alkylene carbonate or alkylene oxide used depend on the desired product. As set forth above, when an alkylene carbonate is used as the alkoxylating agent, a maximum of one alkoxylene unit is added to the phenolic aralkylation polymer, even if an excess amount of alkylene carbonate is used. If a phenolic aralkylation polymer containing both phenolic and aliphatic hydroxyls is to be produced, then the alkylene carbonate can be added in amount sufficient to cap only some of the phenolic hydroxyl groups. The reactivity of phenolic aralkylation polymers that have both phenolic and aliphatic hydroxyl groups can be adjusted by adjusting the amount of these moieties.

When an alkylene oxide is used as the alkoxylating agent, one or more alkoxylene units can be added to the phenolic hydroxyl groups of the phenolic aralkylation polymer. As with alkylene carbonates, alkylene oxides can be added in amount sufficient to cap only some of the phenolic hydroxyl groups. Unlike alkylene carbonates, alkylene oxides allow addition of multiple alkoxylene units to the phenolic hydroxyl groups. This feature permits the preparation of a wide variety of products that differ in the degree of alkoxylation. A large number of alkoxylene units may be desirable for many purposes, including introducing flexibility into coatings, modifying solubility characteristics of the polyols, or reducing viscosity.

The alkoxylation may be performed at any desired temperature. Generally, the alkoxylation occurs at a temperature within the range of about 20° C. to about 250° C., but the required temperature depends significantly on the type of catalyst used. For example, alkoxylation using propylene carbonate and potassium hydroxide as a catalyst is most conveniently performed at temperatures in the 150° C. to 200° C. range. In contrast, propoxylation with propylene oxide using some Lewis acid catalysts can be performed at room temperature.

After the alkoxylation reaction is complete, insoluble salts or catalysts can be removed, if desired, by any convenient method. In one method, the phenolic aralkylation polymer is simply diluted with mineral spirits and is filtered using a filter aid (e.g., CELITE filter aids, or the like). Vacuum stripping of the mineral spirits gives a purified phenolic aralkylation polymer. In other cases, catalyst chemistry can be modified to cause formation of soluble salts which can remain in the reaction product essentially without deleterious effect.

Complete details on the preparation of many of these compositions are found in copending application Ser. No. 08/501,516, filed Jul. 12, 1995, and copending application Ser. No. 08/562,977, filed Nov. 27, 1995, each of which is incorporated herein by reference.

The following are representative of the phenolic aralkylation polymers that can be produced:

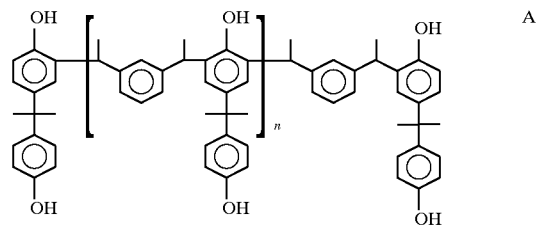

wherein n=0, 1, 2, 3, 4, . . . , up to about 5.

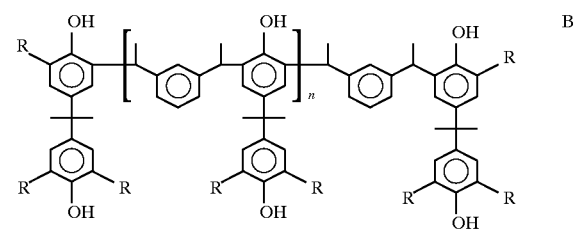

wherein n is as for A above and each R is individually selected from the group consisting of styrene, vinyltoluene, α-methylstyrene, t-butylstyrene, hydrogen, and blends therof.

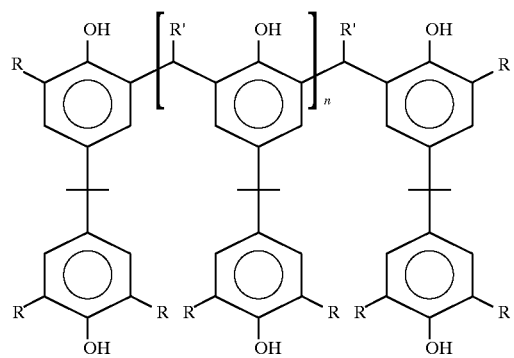

C wherein n is as in A above; R is as in B above; and each R' is individually selected from the group consisting of hydrogen and alkyl moieties having between 1 and about 10 carbon atoms, and blends thereof

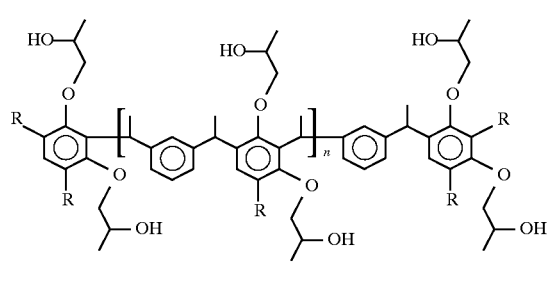

D-1 and

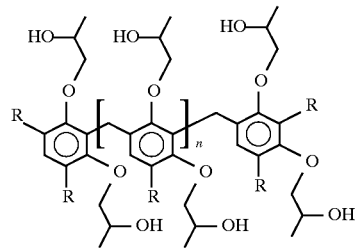

D-2 wherein n is as in A above and R is as in B above. The catechol- and hydroquinone-based analogues of these polymers also are preferred phenolic polymer compounds.

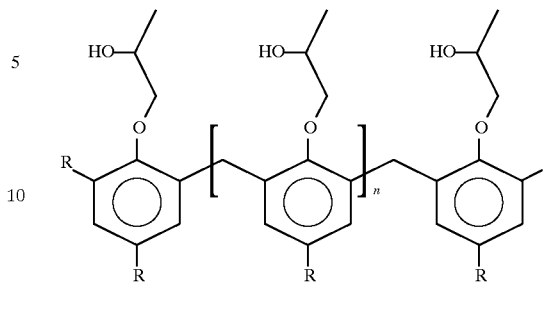

E wherein R is as in B above and n=0, 1, 2, 3, 4, . . . , up to about 10.

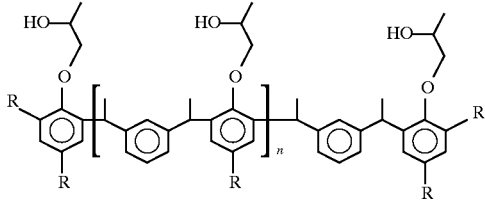

F wherein R is as in B above and n is as in E above.

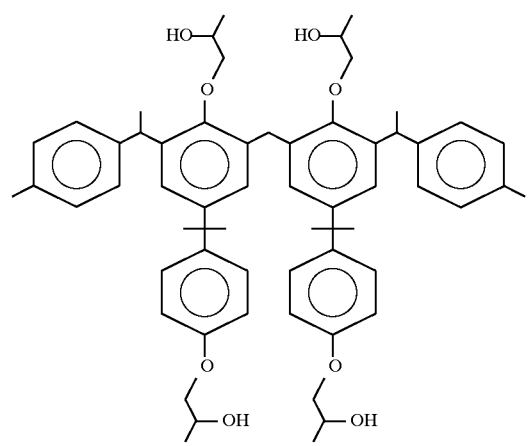

G

-continued

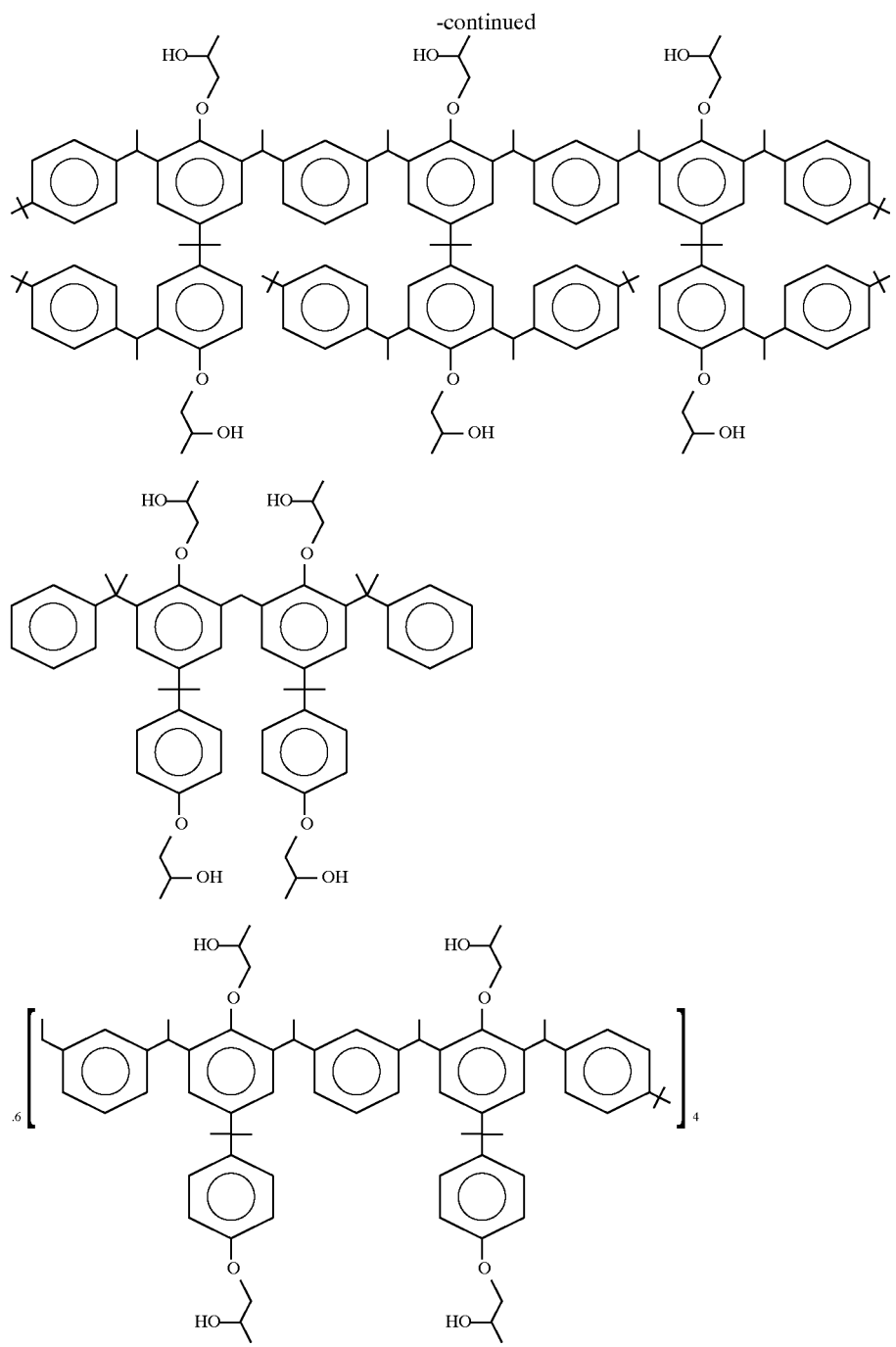

Composition A represents the coupling of bisphenol-A with dlisopropylbenzene to produce a polymer having a functionality of 2+2 n. Unlinked bisphenol-A (functionality of two) will be present in the reaction product. Composition B is a styrenated form of Composition A. Composition C represents phenolic aralkylation polymers represented by Compositions A and B with at least part of the bisphenol-A coupled by formaldehyde, acetaldehyde, and other aldehydes. With the guidance provided, skilled practitioners recognize, from the structures provided herein, how to formulate each of the structures described.

As set forth above, this type of phenolic aralkylation polymer has a low polydispersity as compared to well-known phenol/formaldehyde novolac systems of similar molecular weight. Thus, these polymers can be described and illustrated as discrete molecular structures, and a particular functionality can be ascribed to each such structure. The functionality is defined as the number of reactive hydroxyl moieties on the structure. Thus, Composition A can be said to have a functionality of 6 when n=1. Skilled practitioners recognize that this functionality represents an average functionality of all molecules in the product, and that the product is, in reality, a mixture of molecular structures having functionality above and below the average. However, because such products have low polydispersity, they exhibit a greater tendency to behave as expected in view of the structures expressed.

The present invention is particularly directed to ester derivatives and alkoxylated derivatives of phenolic polyols and to derivatives having both ester modifications and alkoxylation modifications. As set forth above, the invention will be described in detail as it relates to phenolic aralkylation polymers.

In accordance with the invention, the degree of modification is determined so as to impart to the resultant product the desired characteristics. For example, ester-modified product having low residual free hydroxyl functionality is especially suited for grafting onto other polymer coating systems without inducing gelation. Ester-modified products also can be transesterified with reactive oils to incorporate more reactive fatty acid moieties, thus yielding faster drying coating systems. Thus, for these reasons and for other advantages described elsewhere herein, the modified phenolic aralkylation polymer of the invention is useful as a component of a coating system.

For convenience, a summary notation will be used to describe the phenolic aralkylation polymers to be modified in accordance with the invention. This summary notation will indicate only the presence of reactive hydroxyl moieties and moieties between the hydroxyl moiety and a phenolic component. These summary notations for phenolic aralkylation polymers will be identified by the prefix "S." This method is particularly useful for identifying the number of functionalities per molecular unit. The summary notations for phenolic aralkylation polymers A-J above, and the functionality of each, are as follows:

| Summary Notation | Functionality | Identifier |
|---|---|---|
| [OH]$_{n+2}$ / [OH]$_{n+2}$ | 2(n + 2) | S1 |
| [HO—⟨/O⟩]$_{n+2}$ | n + 2 | S2 |
| [HO—⟨/O⟩]$_2$ / [⟨/O⟩—OH]$_2$ | 4 | S3 |
| [HO—⟨/O⟩]$_3$ / [⟨/O⟩—OH]$_3$ | 6 | S4 |
| [HO—⟨/O⟩]$_2$ / [⟨/O⟩—OH]$_2$ | 4 | S5 |

In accordance with one aspect of the invention, hydroxyl moieties are esterified. It has been discovered that the products resulting from the esterification of at least one aliphatic hydroxyl moiety of a phenolic aralkylation polymer with an unsaturated fatty acid is particularly suitable for incorporation in alkyd coating systems. It has further been discovered that these ester products of phenolic aralkylation polymer and unsaturated fatty acid can be further modified, whether by transesterification or by another modification, to enhance their suitability for selected coating systems.

The degree of esterification of the aliphatic hydroxyl moieties, i.e., the number of aliphatic hydroxyl moieties esterified in comparison to the functionality of the phenolic aralkylation polymer molecule, is adjusted in accordance with the guidance found herein to yield esterified phenolic aralkylation polymers having desired characteristics. At least one aliphatic hydroxyl moiety is esterified; all aliphatic hydroxyl moieties on the polymer molecule can be esterified. As described above, phenolic hydroxyl moieties can be esterified by reaction with an anhydride, through transesterification, or by reaction with a lactone.

Because the phenolic aralkylation polymer to be esterified must have an aliphatic hydroxyl moiety, it may be necessary to modify the polymer. Such modification is accomplished by alkoxylation. As described above, use of a plurality of oxyalkaline units to "chain extend" a hydroxyl moiety also can impart desirable characteristics, such as flexibility, solubility, and low viscosity.

Such alkoxylation is carried out as described above. Suitable reactants include propylene oxide, ethylene oxide, isobutylene oxide, and butadiene oxide. As noted, the number of alkyloxide units added to each hydroxyl moiety is selected to impart the desired characteristics. Typically, between 1 and about 10 units, preferably between about 1 and 3 units, are added per hydroxyl moiety. Thus, the following is an example of the alkoxylation reaction:

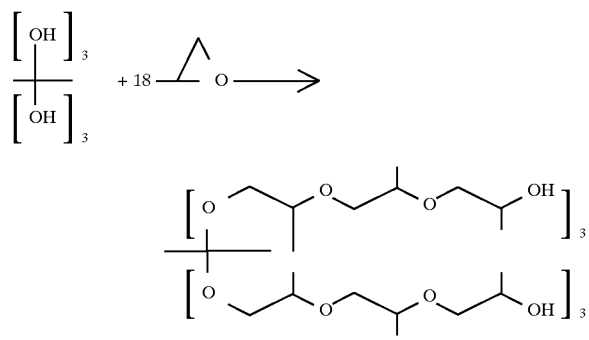

The resultant chain-extended phenolic aralkylation polymer then can be esterified or otherwise modified as set forth below.

The following compositions, although not phenolic aralkylation polymers, are alkoxylated phenolic compounds which, when esterified or otherwise modified in accordance with the invention, form excellent coating systems:

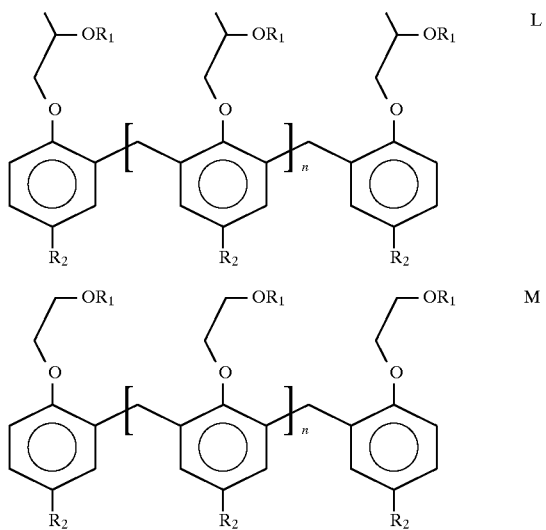

wherein n=1–10;
each $R_1$ is separately selected from hydrogen and TOFA ester, with at least one $R_1$ being the ester; and each $R_2$ is separately selected from t-butyl and p-hydroxycumyl.

Skilled practitioners recognize that fatty acids may be saturated ($C_nH_{2n+1}COOH$) or unsaturated ($C_nH_{2n-1}COOH$, $C_nH_{2n-3}COOH$, and $C_nH_{2n-5}COOH$). In accordance with the invention, any of the commercially available fatty acids can be used to esterify the aliphatic hydroxyl moieties. To incorporate the ester product into an alkyd coating, it is necessary for some of the esterified polymer molecules to be formed by reaction with unsaturated fatty acids. The unsaturation in the carbon chain provides cross-linking sites during formation of the coating. However, if the fatty acid or ester thereof is to be reacted into a coating other than by this cross-linking reaction, a saturated fatty acid or its ester is acceptable.

Skilled practitioners also recognize that seldom is a pure, or single, fatty acid utilized to esterify. Rather, a commercially available blend of fatty acids is used. One such blend is tall oil fatty acid (TOFA). TOFA is the fatty acid fraction of a byproduct stream from sulfate digestion of wood pulp and comprises primarily unsaturated fatty acids. The four primary fatty acids found in TOFA, and the concentrations at which they are found, are palmitic ($C_{15}H_{31}COOH$, 5 percent), stearic ($C_{18}H_{35}COOH$, 2 percent), oleic ($C_{18}H_{33}COOH$, 48 percent), and linoleic ($C_{18}H_{31}COOH$, 45 percent). TOFA is a preferred source of fatty acids.

The inventors also have discovered that esterification with (meth)acrylic acid also provides a product useful in coating systems. The product enables rapid crosslink formation by free radical polymerization in polymer formation.

As with each of the derivatizations of the invention, the degree of esterification of the aliphatic hydroxyl moieties of the phenolic aralkylation polymers can be adjusted to yield a product having preselected characteristics. One or all of the aliphatic hydroxyl moieties can be esterified.

Esterification preferably is carried out under an inert atmosphere, such as nitrogen, and typically in the presence of a solvent. Solvent facilitates removal of byproducts, particularly water, by azeotropic distillation, but esterification can be adequately performed without solvent. Skilled practitioners recognize that both the product and the reactants must be sufficiently soluble in the solvent. Suitable solvents include o-xylene, mixed xylenes, ethylbenzenes, cumene, mineral spirits, and mixtures thereof.

The esterification reaction is carried out under conditions sufficient to achieve esterification. Although completeness of the reaction can be determined in many ways, it is particularly convenient to measure the carboxyl number of the mixture. The acid number is equal to the milligrams of KOH required to neutralize carboxyl moieties per gram of sample solids. Skilled practitioners recognize that the carboxyl number decreases as the concentration of carboxylic moieties (i.e., free, unreacted fatty acid) decreases. Reaction typically is carried out until the carboxyl number, on a 100 percent solids equivalent basis, is less than about 8, preferably less than about six, and more preferably less than about 3. Then, the product is recovered, typically by removing the solvent by distillation.

The esterification reaction typically is catalyzed by a basic composition, such as a metal hydroxide. Lithium hydroxide is preferred. Reaction is carried out at a temperature greater than or equal to 200° C., preferably between about 200°–300° C., more preferably between about 225°–275° C. Under preferred conditions, color body concentration in esterified phenolic aralkylation polymer is minimized, and the degree of phenolic hydroxyl alkylation is increased. In contradistinction, acid catalysis at a lower temperature, i.e., about 100°–150° C., preferably about 110°–125° C, is preferred for esterification with (meth)acrylic acid.

Transesterification

Transesterification of phenolic aralkylation polymer with glyceride oils is a preferred method of incorporating "reactive oils," such as tung oil and linseed oil, with the phenolic aralkylation polymer. "Reactive oils" are so-called because the plural unsaturations in the fatty acid chains provide additional potential cross-linking sites during formation of a coating.

Glyceride oils have the general structure

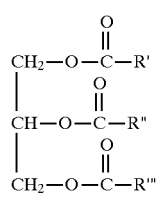

where at least one of R', R", and R'" is a fatty acid residue. The variations in properties between different oils are a function of the variation in fatty acid structure. Because more than one type of fatty acid can be present per oil molecule, the properties of a particular oil can be directly related to the fatty acid composition. Some of the more important glyceride oils and their fatty acid compositions are compared in Table 1 below. This table is taken from P. Oldring, Resins for Surface Coatings, Volume 1, Chapter II ("Glyceride Oils"), p. 49–50. These oils include tung oil, linseed oil, and a range of other oils commonly used in the manufacture of paints and air-drying resins.

| Fatty Acid | Formula | Unsat'n | Linseed Oil | Safflower Oil | Sunflower Oil | Soybean Oil | Tung Oil | Tall Oil |
|---|---|---|---|---|---|---|---|---|
| Palmitic | $C_{16}H_{32}O_2$ | | 6 | 8 | 11 | 11 | 4 | 5 |
| Stearic | $C_{18}H_{36}O_2$ | | 4 | 3 | 6 | 4 | 1 | 2 |
| Oleic | $C_{18}H_{34}O_2$ | 2H | 22 | 13 | 29 | 25 | 8 | 48 |
| Richinoleic | $C_{18}H_{34}O_3$ | 2H | | | | | | |
| Linoleic | $C_{18}H_{32}O_2$ | 4H | 16 | 75 | 52 | 51 | 4 | 45 |
| Linolenic | $C_{18}H_{30}O_2$ | 6H | 52 | 1 | 2 | 9 | 3 | |
| Elaeostearic | $C_{18}H_{30}O_2$ | 6H | | | | | 80 | |
| Licanic | $C_{20}H_{36}O_3$ | 6H | | | | | | |

For convenience, throughout the remainder of this specification, the esterification of phenolic aralkylation polymer with fatty acid will be expressed as follows:

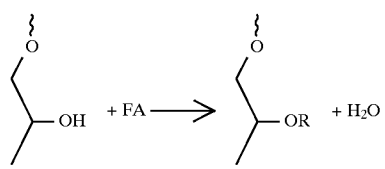

Therefore, reaction of 4 fatty acid moieties with a phenolic aralkylation polymer represented by the abbreviated formula S-4 is expressed as follows:

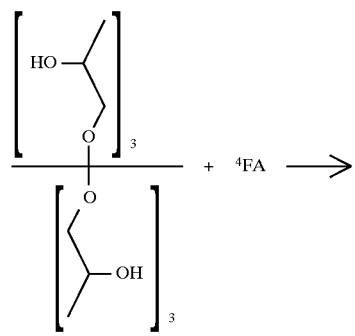

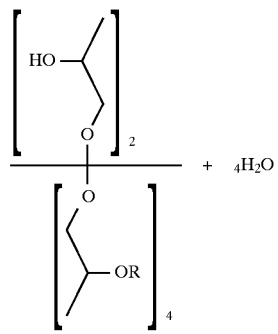

Similarly, the same degree of esterification, i.e., 4 of the 6 aliphatic hydroxyl moieties of the chain-extended phenolic aralkylation polymer of abbreviated form S-5 is expressed as follows:

S-6
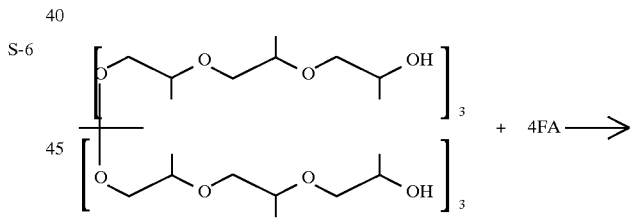

S-7
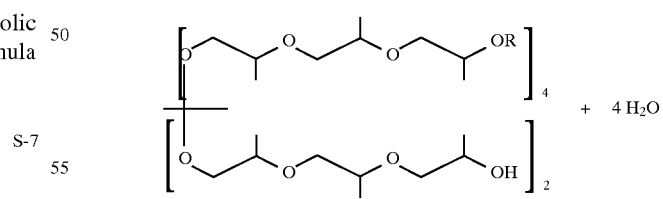

Thus, it can be seen that these abbreviated formulae do not express the exact structure of the product of the esterification reaction, but rather the functionalities thereof.

Esterification of one half of the aliphatic hydroxyl moieties of a 4-functional phenolic aralkylation polymer with TOFA is expressed in this summary notation as follows:

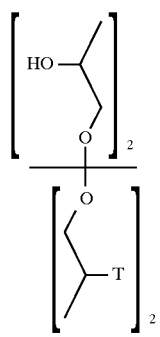

wherein T=TOFA.

It also has been discovered that chain extension can be carried out after partial esterification. In this way, the characteristics and properties of the resultant product can be adjusted. After esterification, chain extension is effective only on aliphatic hydroxyl moieties. Thus, the 2 aliphatic hydroxyl moieties remaining on the product resulting from esterification of 4 positions of a 6-functional phenolic aralkylation polymer can be chain extended in accordance with the invention, as follows:

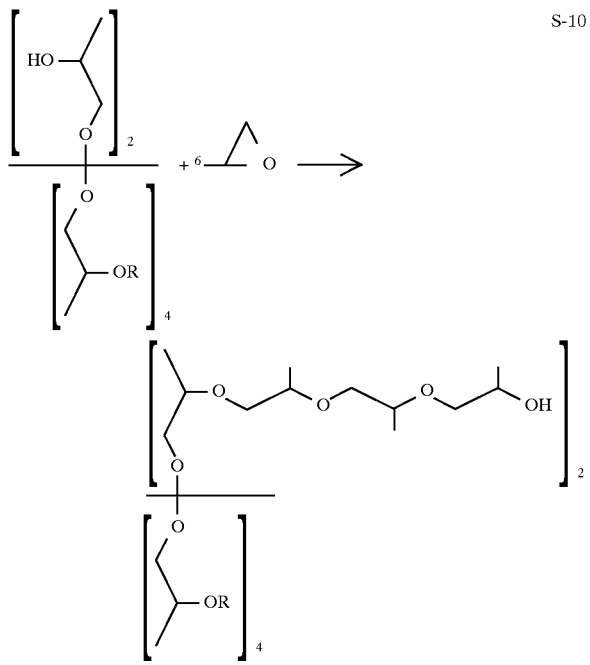

In accordance with the invention, other modified phenolic aralkylation polymers are contemplated. These modifications are not limited to reaction with the aliphatic hydroxyl moieties; rather, any hydroxyl moiety is suitably used for these modifications. For example, in accordance with the invention, a phenol hydroxyl moiety can be reacted with alkylene oxide or alkylene carbonate to yield an aliphatic hydroxyl moiety suitable for esterification. Preferred oxides include ethylene oxide, propylene oxide, isobutylene oxide, and butadiene oxide. Preferred carbonates include ethylene carbonate, propylene carbonate, isobutylene carbonate, and butadiene carbonate.

As described herein, oxides and carbonates having saturated carbon chains will alkoxylate a phenol hydroxyl moiety to yield a hydroxyl moiety pendant from an aliphatic chain. Oxides and carbonates having unsaturated carbon chains will yield an unsaturated chain. As set forth above, diene carbonate also can react with the phenolic aralkylation polymer to provide a pendant carbonate moiety.

In accordance with the invention, butadiene oxide is reacted with phenolic aralkylation polymer in the following ways to provide pendant carbonate moieties:

(1) Direct alkylation of reactive sites on the ring moieties of phenolic aralkylation polymer, as follows:

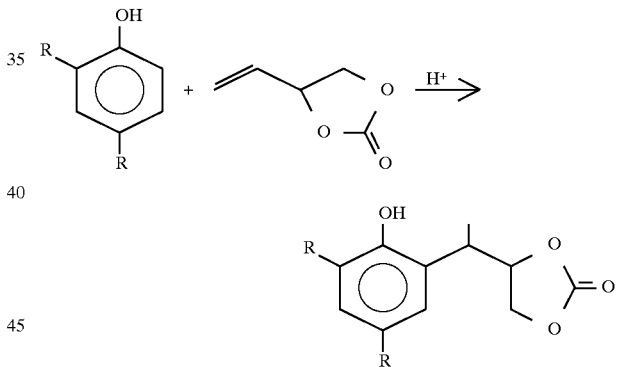

(2) Free radical grafting into polyolefins modified with acrylated phenolic aralkylation "star" polymers.

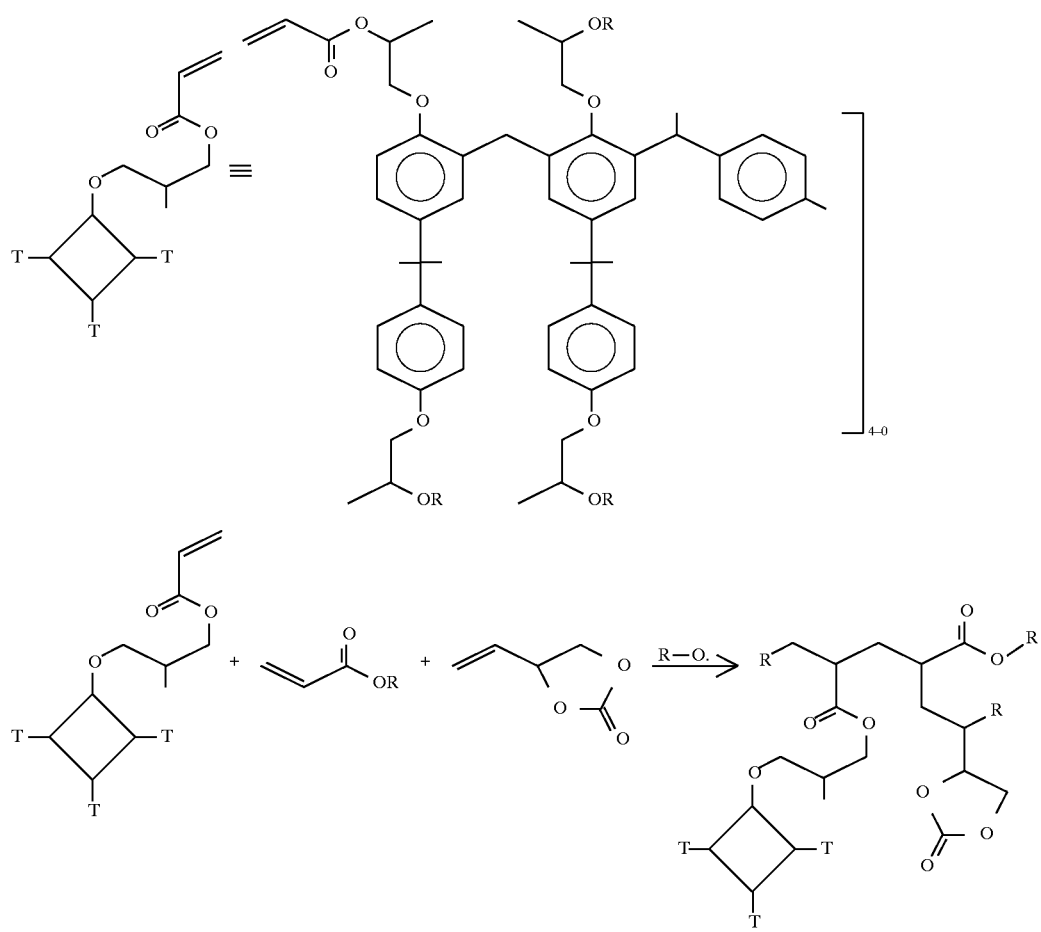
wherein T is as defined above and R=TOFA acid.
Skilled practitioners know how to co-react olefinic monomers of different reactivity.
(3) Grafting onto an ether a-methylene group, as follows:
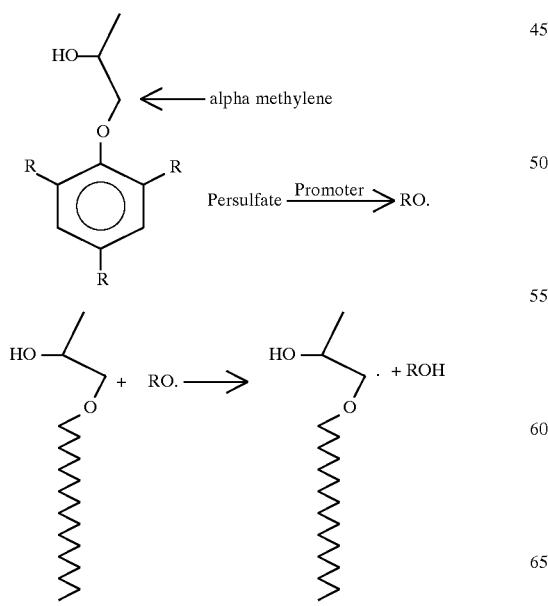
-continued
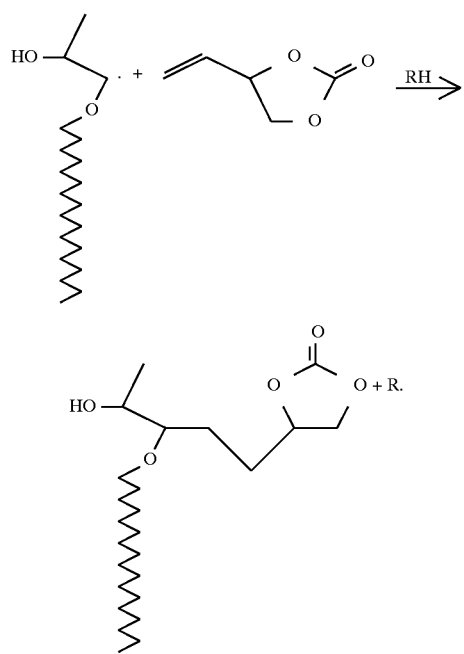
In accordance with the invention, this reaction is conducted on completely alkoxylated phenolic aralkylation polymer using potassium persulfate-type promoters. The reaction is carried out at a temperature between about 60–90° C., preferably between about 75–85° C. Low concentrations of iron or cobalt salts or complexes can promote the reaction at lower temperature.

A carbonate moiety is incorporated onto phenolic aralkylation polymer in accordance with the invention to take advantage of the reactivity of the carbonate moiety with primary and secondary di- and poly-amines at low temperatures to yield highly crosslinked systems. The carbonate/amine linkages are hydroxy urethane linkages which offer both a hydroxyl moiety, which improves coating-to-substrate adhesion, and a urethane linkage, which improves coating toughness characteristics, as known in the art. Additionally, skilled practitioners recognize that the carbonate moiety has low toxicity, which is a distinct advantage over isocyanates, acrylate, and oxirane reactive moieties, all of which are known to exhibit toxicity.

In accordance with the invention, phenolic aralkylation polymer can be derivatized with other functionalities. Typically, such functionalities provide a particularly convenient manner of incorporating phenolic aralkylation polymer into other polymer systems, simultaneously achieving or realizing the advantages thereof.

For example, derivatization by glycerol carbonate introduces a diol ether. Such a moiety conveniently introduces high hydroxyl functionality into the resultant system.

Similarly, derivatization by glycerol acrylate carbonate yields an acrylic-substituted polymer system component particularly suitable for incorporation into acrylate polymer systems. Acrylate functionality can be introduced by reacting glycidyl (meth)acrylate or glycidyl (meth)acrylate carbonate. Both types of reaction systems are reactive with the phenolic hydroxyl moiety in the presence of known oxirane or carbonate catalysis systems and conditions, as set forth in the following reaction formulas:

(1)

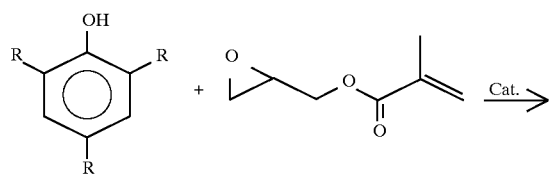

(2)

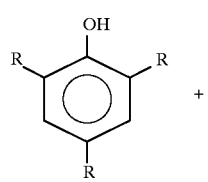

+

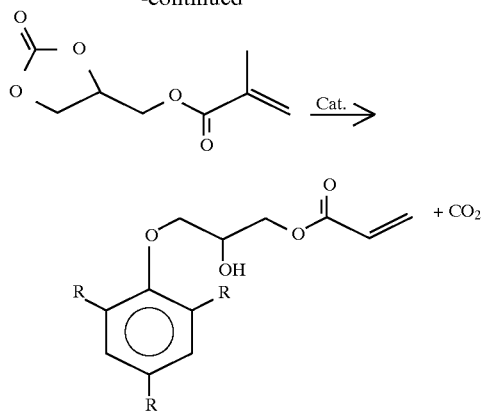

Acrylamide functionality is obtained by derivatization with glycidyl acrylamide or glycidyl acrylamide carbonate, as follows:

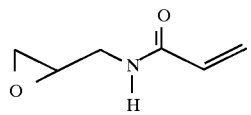

Glycidyl Acrylamide

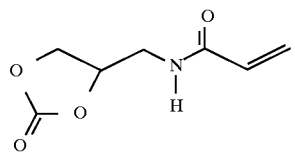

Glycidyl Acrylamide Carbonate

A preferred carbonate-containing phenolic aralkylation polymer of the invention is made by reacting epichlorohydrin carbonate with phenolic aralkylation polymer. Low temperature reaction in the presence of a carbonate buffer is preferred to facilitate the SN-2 nucleophilic displacement of the chloride moiety while leaving the carbonate moiety intact. Those skilled in the art recognize that the path required for such substitution is as set forth below:

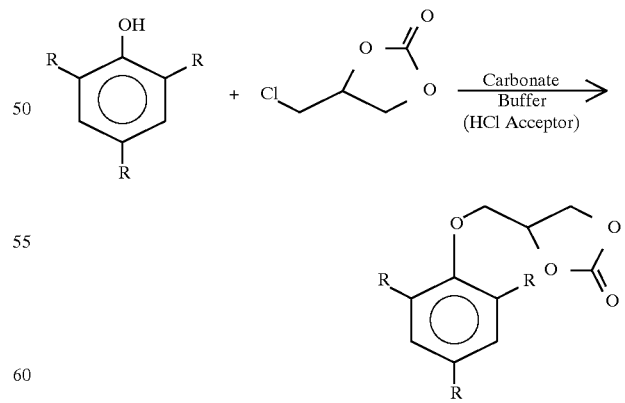

It has been discovered that coating systems comprising the modified phenolic aralkylation polymers of the invention can be provided with desirable characteristics and properties by selecting the type and degree of modification. Not only the functionality, but also the degree of modification, or proportionality thereof, and the identity of the functionalities combined on one molecule affect the use to which the modified molecule is advantageously put. For every type of coating system in which modified phenolic aralkylation polymer is incorporated or to which it is added, the relatively large aromatic "hard block" segments yield improved hardness and better barrier properties.

It has been discovered that ester-modified phenolic aralkylation polymers of the invention form low-melting, low-viscosity coating systems in conjunction with other polymer systems. Viscosity can be lowered even further by alkylene oxide chain extension. Propylene oxide is preferred to provide highest solubility in non-polar solvents. Such modified molecules are compatible with organic solvents and, in particular, "safe" (i.e., environmentally friendly) solvents, such as mineral spirits.

These low-melting, low-viscosity molecules also are ideally introduced into water-borne coating systems. Such systems are capable of coalescing with only minimal addition of coalescing solvents. The "hard block" character of the modified polymers of the invention, when combined with the "soft block" characteristics of the coating system into which it is incorporated, leads to excellent coating performance.

The excellent compatibility of esterified phenolic aralkylation polymers of the invention with other coating systems results in a new class of coating systems which have excellent water resistance while maintaining excellent barrier properties, adhesion, and other desirable characteristics. The presence of fatty acid esters greatly increases the solubility of thus-modified molecules in organic solvents. When air-dried, the resultant coating is inherently hydrophobic. The aromatic moieties greatly enhance the barrier characteristics and the adhesiveness to both substrates and prior layers of the coating system.

Retained hydroxyl functionality affords the opportunity to incorporate the modified molecule of the invention into epoxy-, acrylate-, polyester-, polyurethane-, or polyester urethane-based coating systems. Hydroxyl fanctionalities also can be used as a base for a chain-extending reaction with di- and poly-isocyanates and di- and poly-carboxylic acids. These extended-chain polymers also are suitable for use in combination with environmentally safe solvents such as mineral spirits and with metal drying systems to form coating systems.

In particular, a two-step reaction of partly-esterified phenolic aralkylation polymer, first with a minor quantity of di- or poly-carboxylic acid, then with a di- or poly-isocyanate, produces an extended-chain resin suitable for introduction into a coating system or for formation of a coating itself The quantity of carboxylic acid is sufficient to produce a phenolic aralkylation polymer of desired molecular weight. Then, using isocyanates to incorporate alkyd resin components to partially esterified phenolic aralkylation polymer results in a coating system that yields coatings having rapid hardness development, excellent scratch resistance, and high impact performance.

Modified phenolic aralkylation polymers having relatively limited average secondary aliphatic hydroxyl functionality, i.e., up to about 2.5, preferably between about 0.8 and 2.0, free secondary aliphatic hydroxyl moieties per molecule, or free primary aliphatic hydroxyl moieties per molecule if modified with ethylene oxide or ethylene carbonate, are particularly suited for grafting on to other polymer systems without causing gelation. Such polymer systems are useful in forming coating systems that are air-drying and are water dispersible.

Coating systems comprising esterified phenolic aralkylation polymers of the invention require significantly lower volatile organic content (i.e., solvent) than known phenolic-modified alkyd coatings. Thus, coatings comprising modified polymer of the invention can have higher solids concentration and lower viscosity. Importantly, such coating systems can be water-borne, thus ameliorating environmental damage and simplifying application and clean-up.

Ester-exchange products, in which a TOFA-modified phenolic aralkylation polymer is trans-esterified with reactive oils, such as tung oil (which typically comprises about 80 percent elaeostearic ($C_{18}H_{30}O_2$) acid), incorporate more reactive fatty acid moieties. These reactive fatty acid moieties afford a higher drying rate in an air-dried coating system.

The ester-modified phenolic aralkylation polymer of the invention typically is grit-free, i.e., is devoid of salts of the catalyst components, and has a light color. Although the inventors do not wish to be bound by theory, the fatty acid components apparently solubilize the salt components. Therefore, such polymers are suitably incorporated into coating systems. Because esterified phenolic aralkylation polymer is compatible with solvents used to carry alkyd and uralkyd coating systems, it is a convenient additive to such coating systems. The resultant uralkyd coating systems have good clarity, gloss, hardness, and toughness.

The highly aromatic nature of the modified phenolic aralkylation polymer of the invention makes it especially suitable as a UV absorber for, e.g., exterior alkyd clear coatings. Further, because the aromatic phenolic moieties are reacted into the resultant polymer network, there is no "bleed out"-type degradation of the coating as is commonly found in aromatic phenolic-containing systems. The highly aromatic nature also provides increased resistance to degradation by water. Further, esterified phenolic aralkylation polymer provides excellent adhesion not only with substrates but also between coats.

Other applications for suitable esterified phenolic aralkylation polymer include tackifier for acrylate systems cured by exposure to UV radiation; epoxy alkyd precursor components (alkyds) for moisture-resistant abrasives and for water-borne alkyd coatings.

Multiply-functional modified phenolic aralkylation polymers of the invention are particularly useful as compatiblizer between two systems that are or would otherwise be incompatible. For example, such multiply-functional modified phenolic aralkylation polymer of the invention could be grafted into coating systems comprising polymethylol melamine systems, such as Cymel 303, or phenolic methylol systems. Thus, the modified molecule serves as a compatibilizer to couple normally incompatible agents into alkyd type coating systems and adhesive systems. In these systems, the aliphatic hydroxyl moieties form ethers with the melamine or phenolic methylols.

Ester-modified phenolic aralkylation polymers of the invention are cost-effective. In particular, formaldehyde-inked and non-aryl diolefin-linked systems based on bisphenol A, bisphenol F, or dihydroxybenzenes styrenated with low cost styrene derivatives (preferably α-methylstyrene and ring-substituted methyl styrenes) and alkoxylated with alkylene carbonate (preferably propylene carbonate), when esterified with unsaturated fatty acids, preferably TOFA, yields coating system components that enhance hardness and other performance attributes and characteristics of alkyd-based coatings. The fatty acid moieties increase the solubility and lower the viscosity of coating systems utilizing non-polar solvents. Thus, a "safe" solvent such as mineral spirits can be used as the sole diluting solvent in the coating system.

In particular, alkoxylated versions of phenolic aralkylation polymers of the types represented by Compositions A, B, C, D-1, and D-2, and phenolic aralkylation polymer H, are particularly useful for ester exchange with unsaturated tri-glyceride such as tung oil and linseed oil.

The resultant polyol ester mixture comprises mono-, di-, and tri-glyceride of the parent unsaturated glyceride and the fatty acid ester exchange products of the phenolic aralkylation polymer. The resultant products exhibit excellent hydrocarbon (mineral spirits) solubility. This is believed to be due to the incorporation of styrenes, such as t-butyl styrene, which tend to increase the solubility of the resultant pre-polymer systems in non-polar solvent.

Ester exchange products of this kind are capable of air-drying to cured coatings, showing reasonably good hardness. Further modification of these pre-polymers involves their further chain extension through reaction of the ester exchange reaction mixture with diisocyanates. These products show excellent hardness and durability and result in materials which can be blended into normal alkyd systems to increase toughness and hardness as well as inter-coat adhesion and improved adhesion to metal substrates.

Alkoxylated phenolic aralkylation polymers of the types derived from polymers represented by Compositions B and C suitably are added to the glycerol/tri-glyceride ester exchange reaction mixture so that some of the unsaturated fatty acids are exchanged to the phenolic aralkylation polymer. The resultant mixture then can be used to produce alkyd or uralkyd coating systems. The distinct advantage here lies in the ability to incorporate some of the phenolic aralkylation polymer into the polyester, polyester urethane, or polyurethane chain-extending backbone formed during the chain extension. These harder segments of the phenolic aralkylation polymer greatly increase the hardness potential of the resultant coating while maintaining excellent mineral spirits solubility. In addition, higher levels of resultant cured polymer toughness can be obtained. In such coating systems, substitution of penetaeryrthritol for glycerol also yields a preferred type of coating system. Preferably, pentaerythritol-containing systems are driven to maximize the production of pentaerythritol diesters of fatty acids.

A phenolic aralkylation polymer having 2 hydroxyl functionalities can be incorporated as a diol in either alkyd ester or uralkyd ester coating systems. The resulting highly aromatic diol increases hardness of the coating while allowing significant chain extension. With this type of modification, high increase of chain extension can be achieved, thus providing better toughness and hardness for the resultant coating system.

Each of the phenolic aralkylation polymers in which the phenol hydroxyl moieties are converted to alkoxyl functionalities are suitably used as "direct drop-ins" to either uralkyd or alkyd coating systems. The hardness of the phenolic aralkylation polymer serves to provide durability in the resulting system similar to durability found in phenolic-modified alkyds and uralkyds. The clear advantage of the phenolic aralkylation polymers of the invention lies in the fact that the phenolic hydroxyl moieties are "blocked" by the alkoxylate moieties. These blocked materials show much better UV durability without discoloring the coating. Systems of this type maintain the advantage of good weather-ability seen in phenolic-modified alkyds and uralkyds.

An additional advantage is the much faster auto-oxidative cure rate of the alkoxylated phenolic aralkylation polymer of the invention, as compared to the cure rate of known systems containing underivatized phenolic hydroxyl moieties. The increase in rate is due to the lack of phenolic inhibition of the curing process.

Phenolic aralkylation polymers represented by Composition B and alkoxylated versions of Compositions A–C desirability are reacted with diacids to produce diacid functional polyols. These polyol materials can be grafted into normal alkyd pre-polymers with the phenolic aralkylation polymer component being incorporated into the polyol backbone. A further advantage of these carboxyl-functional systems lies in their potential for curing with epoxide systems.

Similarly, polyols can be formed by reaction of these polymers with epoxies, phenolic resoles, melamines, diisocyanates, and the like.

In accordance with the invention, unsaturated fatty acids are directly esterified to the phenolic aralkylation polymer, with subsequent chain-extension by reaction with diacids, diisocyanates, diepoxides, and combinations thereof Skilled practitioners recognize that dfisocyanates are appropriately used if a deficiency of dicarboxylic acid is first used to form the polyester, as the hydroxyl moieties react preferentially with the more-reactive dfisocyanates to achieve rapid chain growth. In contrast, diepoxides are most efficient in reducing free carboxyl number in reactions in which a near-stoichiometric quantity of diacid reactant is used, as it is more expeditious to form epoxy linkages that it is to react with remaining hydroxyl moieties. Because of the higher than two functionality potential of phenolic aralkylation polymers, it is possible to incorporate a multiplicity of reactive functionalities into a single polymer system.

Of particular interest is the grafting of partially esterified phenolic aralkylation polymer into other polyol systems to generate star polymer precursors, in which the nucleus of the resin system radiates to arms containing unsaturated fatty esters. Such a system would have extremely low viscosity, excellent mineral spirits solubility, and a potential for rapid reaction into cured systems.

EXAMPLES

The following examples further describe the invention, but should not be considered limiting in any way.

Example 1 Preparation of a 6-Functional Isopropoxylated Phenolic Aralkylation Polymer Having 4 Hydroxyl Functionalities Esterified by TOFA A. Preparation of a $^6$-functional phenolic aralkylation polymer A standard resin kettle was charged with bisphenol-A (565 grams) and heated to 120° C. At this point, t-butylstyrene (330 grams) was added. Methane sulfonic acid (70 percent, 0.7 grams) was added slowly over five minutes. The reactor charge was allowed to exotherm to 150–160° C. and divinylbenzene (80 percent, 268 grams) was added over 15 minutes at 150–160° C. After completion of the divinylbenzene addition, the temperature was maintained for five minutes before the remaining t-butylstyrene was added over twenty minutes with the reactor maintained at 150° C. Heating was continued for ten minutes after the addition was complete. Then, aqueous potassium hydroxide (50 percent solution, 1.8 grams) was added and a vacuum applied to remove water from the system.

B. Isopropoxylation

Propylene carbonate (505 grams) was added after the temperature was adjusted to 170° C. The mixture was heated at 170° C. for fourteen hours in an open system to vent carbon dioxide generated by the reaction. Analysis by FTIR indicated greater than 90 percent conversion of propylene carbonate. Mineral spirits (450 grams) was added, and the mixture heated to 170° C. The hot mixture was filtered through a 30 micron fritted glass funnel and CELITE 545 filter aid. The filtrate was recharged to the reactor, heated to between about 160 and 170° C., and distilled under vacuum (twenty-seven inches Hg) to remove all solvent. The mixture was cast onto an aluminum pan and flaked.

The molecular weight of the resultant phenolic aralkylation polymer was 2183, yielding an equivalent molecular weight (molecular weight per hydroxyl functionality) of 364.

C. Esterification by TOFA

Into a stirred 1-liter reactor blanketed with nitrogen were placed 300 grams (0.14 moles) of 6-functional isopropoxylated phenolic aralkylation polymer of part B, 156 grams (0.56 (=4×0.14) moles) of TOFA (molecular weight 284), and 100 grams of o-xylene. The mixture was heated to 250° C. and 0.04 grams of lithium hydroxide monohydrate catalyst were added. A Dean-Stark trap on the reactor was filled with o-xylene and reflux was maintained at 245° C.

The starting mixture had a carboxyl number of 59 (TOFA having a carboxyl number of 180 comprises 32.6 weight percent of the mixture). Reaction was allowed to continue at 245° C. until the carboxyl number equaled 2. The o-xylene was removed by distillation.

The resultant product was a clear, light yellow (Gardner 1.5), highly viscous liquid infinitely soluble in mineral spirits.

Example 2 Preparation of a 6-Functional Isopropoxylated Phenolic Aralkylation Polymer Having 2.5 Hydroxyl Functionalities Esterified by TOFA and 1 Hydroxyl Functionality Esterified by Tung Oil Three hundred grams (0.14 moles) of the isopropoxylated phenolic aralkylation polymer of Example 1 B were charged to a 1-liter stirred reactor blanketed with nitrogen. TOFA (98 grams, 0.35 (2.5×0.14) moles) and 100 grams o-xylene were charged, and the mixture heated to 250° C. Catalyst (0.04 grams of lithium hydroxide monohydrate) was added, the Dean-Stark trap was filled with o-xylene, and reaction was allowed to proceed until the carboxyl number was reduced to 6. A quantity of tung oil sufficient to substitute 1.0 aliphatic hydroxyl moieties with fatty acid from 0.5 molar equivalents of tung oil was added to the mixture and reacted at 230° C. The quantity of tung oil was 60 grams (0.07 moles). This amount of tung oil is assumed to have one-half of it's weight of organic acid moieties transferred. After about two hours reaction, the viscosity reached a predetermined value, as determined by using a spatula to draw resin "strings" from a room-temperature sample, and the o-xylene was distilled from the reaction mixture.

The resultant product was a highly viscous liquid having Gardner 2 color and infinite solubility in mineral spirits.

Example 3 Preparation of 6-Functional Isopropoxylated Phenolic Aralkylation Polymer Transesterified by 2.3 Functionalities of Tung Oil A. Preparation of 6-functional phenolic aralkylation polymer.

A standard one-liter resin kettle was charged with bisphenol-A (212 grams) and 50 grams of o-xylene. Heating the mixture to 140° C. produced a clear solution of completely dissolved bisphenol-A in o-xylene. After methane sulfonic acid (70 percent, 0.25 grams) was added, divinylbenzene (99.7 grams, 80 percent) was added over fifteen minutes while maintaining the reaction mixture at 150° C. After divinylbenzene addition, the reactor temperature was held at 150° C. for 15 minutes. Then, 298 grams of 95 percent p-t-butylstyrene was added over 30 minutes while maintaining the reactor temperature at 150° C. After p-t-butylstyrene addition, the reactor was held at 140° C. for one hour. Next, aqueous potassium hydroxide (50 percent solution, 1.0 grams) was added.

B. Isopropoxylation

Propylene carbonate (190 grams) was added after the temperature of the reaction mixture was adjusted to 170° C. The mixture was heated at 170° C. for fourteen hours in an open system to vent carbon dioxide generated by the reaction. The reaction was deemed complete when no further $CO_2$ evolution was observed. After dilution with mineral spirits, the reaction mixture was filtered, solvent was removed by distillation, and the product flaked in the matter previously described.

C. Transesterification

One hundred seventy grams (0.08 moles, 0.48 equivalents) of the isopropoxylated product of Part B of this example, two hundred grams (0.228 moles, 0.68 equivalents) tung oil (molecular weight 875), and 50 grams o-xylene were charged to a stirred 1-liter nitrogen-blanketed reactor. The mixture was heated to 145° C., at which temperature 0.5 grams potassium hydroxide aqueous solution (50 weight percent) was added. Heating was continued until the temperature reached 230° C., at which temperature reaction was allowed to continue for about 1.5 hours. The resultant mixture of glycerides and esterified phenolic aralkylation polymer is a light-color, high-viscosity o-xylene solution.

Example 4 Preparation of Uralkyd Coating Systems

The TOFA- and tung oil-esterified phenolic aralkylation polymers of Examples 1–3 were used to prepare uralkyd coating systems. Coatings made therefrom were tested for color, hardness, and other characteristics.

The following proportions were used (all quantities in grams):

| Sample | A | B | C | D | E* |
|---|---|---|---|---|---|
| Alkyd Base (McWhorter Technologies, 127-0547) | 5.0 | 5.0 | 5.0 | | |
| Isophoronediisocyanate (IPDI) | 1.0 | 1.0 | 1.0 | 0.25 | 0.25 |
| Mineral Spirits | 1.0 | 1.0 | 1.0 | | |
| Esterified Phenolic Aralkylation Polymer | | | | | |
| Identity (Example) | 3 | 1 | 1 | 2 | 2 |
| Quantity | 2.0 | 2.0 | 2.0 | 5.0 | 5.0 |
| Phenolic Aralkylation Polymer | | | | | |
| Identity (Example) | | | 1 | | |
| Quantity | | | 2.0 | | |
| Drying Time (Touch Dry), Hours | 1.5 | <4.0 | 1.0 | 0.5 | 0.5 |
| Gardner Color | 2.5 | 2.0 | 2.0 | 1.5 | 1.5 |
| 6-day Pencil Hardness | B | B | B | B | B |

Note - *Product E is a mix of equal proportions of Sample D and Flecto commercial coating "Verathane V-90."

In each preparation, the alkyd base, isophoronedfisocyanate, and mineral spirits are mixed and heated with 1 drop of dibutyl tin dilaurate. The esterified phenolic aralkylation polymer then is added, and the mixture heated to 78° C. and held there for about 90 minutes.

A quantity of mineral spirits sufficient to reduce the solids concentration to 50 weight percent is added. Then a cobalt/manganese dryer package such as is known in the art is added. A coating is formed by drawing down on steel Q panels to a 1.0 mil dry coating thickness. The data illustrate that coatings comprising TOFA-esterified and tung-oil transesterified phenolic aralkylation polymers of the invention produce excellent coatings.

Example 5 Uralkyd Coating System Based on 4-Functional Phenolic Aralkylation Polymer A. Preparation of a 4-functional aralkylation polymer A standard resin kettle equipped with nitrogen blanketing capability was charged with 456 grams bisphenol-A and 100 grams of o-xylene. Heating to 140° C. produced a clear solution of completely dissolved bisphenol-A in o-xylene. Methane sulfonic acid (70 percent, 0.50 grams) was added. At this point, 320 grams of p-t-butylstyrene was added over ten minutes at a temperature of 150° C. At completion of the initial p-t-butylstyrene charge, addition of a quantity of divinylbenzene (80 percent, 162.5 grams) was initiated at a rate sufficient to complete addition in 15 minutes without allowing the temperature to exceed 160° C. At completion of the divinylbenzene addition, the remaining p -t -butylstyrene (320 grams) was added over a period of 15 minutes. At the end of the second styrene addition, heating was continued for 15 minutes at 150° C. Next, aqueous potassium hydroxide solution (50 percent, 1.5 grams) was added.

B. Isopropoxylation

Propylene carbonate (408 grams) was added after the temperature of the reaction mixture was adjusted to 170° C. The mixture was heated at this temperature for fourteen hours in an open system under a nitrogen blanket to vent carbon dioxide generated by the reaction. The reaction was completed when the normalized IR peak for the carbonate carbonyl indicated greater than 95 percent conversion. After dilution with mineral spirits, the reaction mixture was filtered, the solvent was distilled out, and the product was flaked in the manner described above.

C. Preparation of a Coating System

A first solution was prepared by dissolving 50 grams of the product of Part B of this example in 50 grams mineral spirits and heating to 150° C. Fifty grams of a commercial alkyd base (McWhorter Technologies 127-0547) were dissolved in 50 grams of mineral spirits to form a second solution. Seventeen grams of isophorone-diisocyanate were added to the second solution. Then, the second solution and four drops of dibutyl tin dilaurate were added to the first solution. The resultant mixture was heated to 78° C. for 90 minutes. Then, three grams of butanol were added and heating was continued for an additional 30 minutes. The solution then was diluted to 50 percent solids by addition of mineral spirits, and a cobalt/manganese dryer system was added. Characteristics of the resulting coating system are summarized below.

Example 6 Coating Systems Comprising Esterified Isopropoxylated 6-Functional Phenolic Aralkylation Polymer Esterified isopropoxylated 6-functional phenolic aralkylation polymer was prepared in accordance with the method set forth in Examples 1 and 2. These compositions of the invention then were incorporated into coating systems, as follows:

| Sample | A | B | C | D |
|---|---|---|---|---|
| Esterified Phenolic Aralkylation Polymer | | | | |
| Identity (Example) | 2 | 2 | 1 | 1 |
| Quantity (grams) | 50 | 50 | 50 | 50 |
| Mineral Spirits (grams) | 40 | 40 | 30 | 30 |
| Dibutyl tin dilaurate (drops) | 3 | 3 | 5 | 3 |
| Isophoronediisocyanate (grams) | 4 | 10 | 7 | 5 |
| Alkyd Base | | 20 | | |
| Material of Example 5, Part C | | | 30 | |
| n-butanol (grams) | 2 | 2 | 2 | 2 |

All components except n-butanol were charged to a stirred reactor and heated to about 78° C. This temperature was held for about 100 minutes. Then, the butanol was added.

Coatings were formed from the compositions identified as 5 and 6 A–D in accordance with the techniques described in Example 4. The table below summarizes the results of these tests. The test panels were prepared by drawing down the coating with the described dryer packages on steel Q panels. Three wet coating thicknesses were applied to allow determination of coating hardness as a function of thickness. The dry coating thickness was confirmed by an Elcometer® eddy current coating thickness measurement device. The results indicate the exemplary characteristics of coatings comprising modified phenolic aralkylation polymers of the invention.

| SWARD ROCKER (DOUBLE ROCKS) HARDNESS (10 DAY) AS A FUNCTION OF COATING THICKNESS | | | | | |
|---|---|---|---|---|---|
| Coating Thickness, mils | 0.4 | 0.8 | 1.2 | 1.6 | 3.0 |
| Example 5 | 35 | 27 | 23 | 20 | |
| Example 6A | 33 | 27 | 22 | 17 | |
| Example 6B | 23 | 18 | 16 | 14 | |
| Example 6C | | | 24 | 20 | 16 |
| Example 6D | 30 | 23 | 18 | 14 | |

Example 7 Preparation of a Low-Cost 4-Functional Phenolic Aralkylation Polymer Esterified with 2 TOFA A. Preparation of 4-functional phenolic aralkylation polymer Using a standard 5000 gram glass kettle with supporting hardware, bisphenol-A (2425 grams) was charged along with 1255 grams α-methyl styrene. The starting raw materials were mixed and heated to 120° C. Methane sulfonic acid (three grams) was charged and the reaction mixture was allowed to exotherm to 160° C. under control The reaction was allowed to continue at this temperature for 30 minutes. The kettle was set to atmospheric reflux and allowed to cool to 120° C. Formaldehyde addition (a total of 318 grams of a 50 wt percent aqueous solution) was programmed so as to allow the kettle to reflux and maintain a rolling boil. The reaction was allowed to continue for 30 minutes after all formaldehyde had been charged. The kettle then was set to vacuum distillation and distilled under full vacuum (27–30 in Hg) until the kettle temperature reached 140° C. The kettle was set to atmosphere reflux and 50 percent potassium hydroxide solution (15 grams) was charged and allowed to mix for 5 minutes.

B. Isopropoxylation

Propylene carbonate (1299 grams) was added to the kettle and the material mixed and heated to 180–190° C. During the isopropoxylation reaction, the carbon dioxide generated was vented. The kettle was held at 180–190° C. until the PC number by FTIR method was 1 or less, thus indicating a polycarbonate conversion of greater than 90 percent.

The resultant composition was the structure represented by formula I, repeated here:

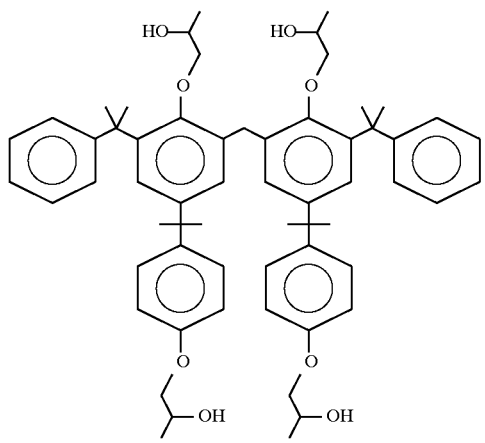

I

C. Esterification

TOFA (1796 grams) was charged to the kettle and the kettle heated to 225–235° C. The TOFA was allowed to react until the acid number was between about 1 and 4. The resultant structure is represented by the following formula:

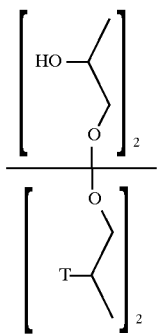

To distinguish this molecule from other molecules of the invention described in this example, this structure will be shown as follows:

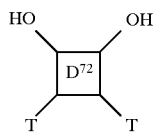

D. Chain extensions with another phenolic aralkylation polymer, with alkyd resin, and with alkyd base Each chain extension was carried out in a 400 ml beaker located in a constant temperature oven regulated to 78° C. All coating systems were adjusted to 50 weight percent solids and had a dryer package added prior to coating evaluation, in accordance with the techniques described in the examples.

1. Coating System 7D1

Esterified composition of invention from Part C of this example (10.6 grams) was added to the beaker together with 5.6 grams of Composition of the Invention J, the structure of which is repeated below:

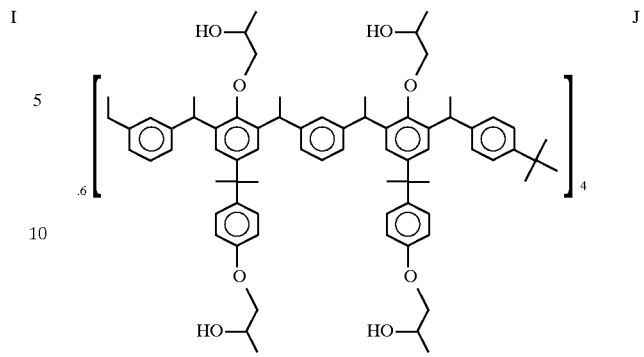

J

Mineral spirits (18.7 grams) were added and the mixture was heated to 90° C. and stirred to ensure complete dissolution. The contents then were cooled to 80° C. and 2 drops of dibutyl tin dilaurate were added. Isophoronediisocyanate (1.6 grams) was mixed in. The beaker was allowed to sit in the 78° C. oven for two hours.

The beaker then was removed from the oven and 5.5 grams of a commercially available alkyd resin (McWhorter 057-4368) and 4.5 grams mineral spirits were added. The components were heated to 80° C. and mixed. Additional dibutyl tin dilaurate (2 drops) and isophoronediisocyanate (1.6 grams) were mixed in. The contents of the beaker were allowed to react for an additional two hours in the 78° C. oven.

The structure of the resulting coating of the invention may be illustrated by the following formula, wherein U represent a urethane-type linkage resulting from the joining of two hydroxyl moieties by reaction with a diisocyanate and ~~~ represents the alkyd resin.

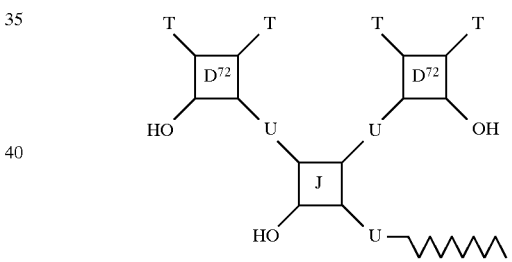

2. Coating System 7D2

Esterified composition of the invention from Part C of this example (15.5 grams) was charged to the reaction beaker together with Composition J (8.0 grams) and 26.8 grams mineral spirits. After ensuring complete dissolution of the reactants by heating to 90° C., the beaker was cooled to 80° C. and 2 drops dibutyl tin dilaurate and 2.3 grams isophoronediisocyanate were mixed in. The beaker was placed in the 78° C. oven for two hours.

The beaker then was removed from the oven and 11.3 grams of a commercially available alkyd base (McWhorter 127-0547) and 8.9 grams mineral spirits were mixed in. The alkyd base described differs from the alkyd resin used in Part D1 of this example in both molecular weight and hydroxyl equivalent weight, with the base lower in both respects. Additional dibutyl tin dilaurate (2 drops) and isophoronediisocyanate (2.2 grams) were added. The beaker was mixed and allowed to react for two additional hours at 78° C.

The resultant structure is identical to that set forth in example 7-D-1 above, wherein the symbol ~~~ represents the alkyd base rather than the alkyd resin.

3. Coating System 7D3

Composition of the invention J (3.5 grams), 19.6 grams of commercial alkyd base from McWhorter (127-0547), and 25.9 grams mineral spirits were added to a reaction beaker, heated to 90° C., and mixed to ensure complete dissolution. Dibutyl tin dilaurate (2 drops) was added, the beaker was cooled to 80° C., and 1.9 grams isophoronediisocyanate was added. The beaker was placed into a constant temperature oven for 120 minutes at 78° C. After the initial reaction in which the alkyd-linked phenolic aralkylation polymer was formed, 13.2 grams of the composition of the invention of Part C of this example, 8.6. grams of mineral spirits, and 2 drops of dibutyl tin dilaurate were added to the reaction mixture together with 1.9 grams of isophoronedilsocyanate. The reaction beaker was heated for an additional 120 minutes at 78° C.

The structure of this coating system of the invention can be represented as follows:

4. Coating System 7D4

To the beaker were added 3.9 grams J, 22.1 grams alkyd base, and 21.6 grams mineral spirits. After the beaker was heated to 90° C. to ensure dissolution of reactants, 2 drops dibutyl tin dilaurate were added. The beaker then was cooled to 80° C., 2.2 grams isophoronediisocyanate were charged, and the beaker was placed in the 78° C. oven for two hours.

To a second beaker 7.8 grams J, 14.9 grams composition of invention 7-1, and 25.0 grams mineral spirits were charged and heated to 90° C. to ensure dissolution, then cooled to 80° C. Two drops of dibutyl tin dilaurate and 2.2 grams isophoronedilsocyanate are mixed in. The beaker is placed in the oven at 78° C. for two hours.

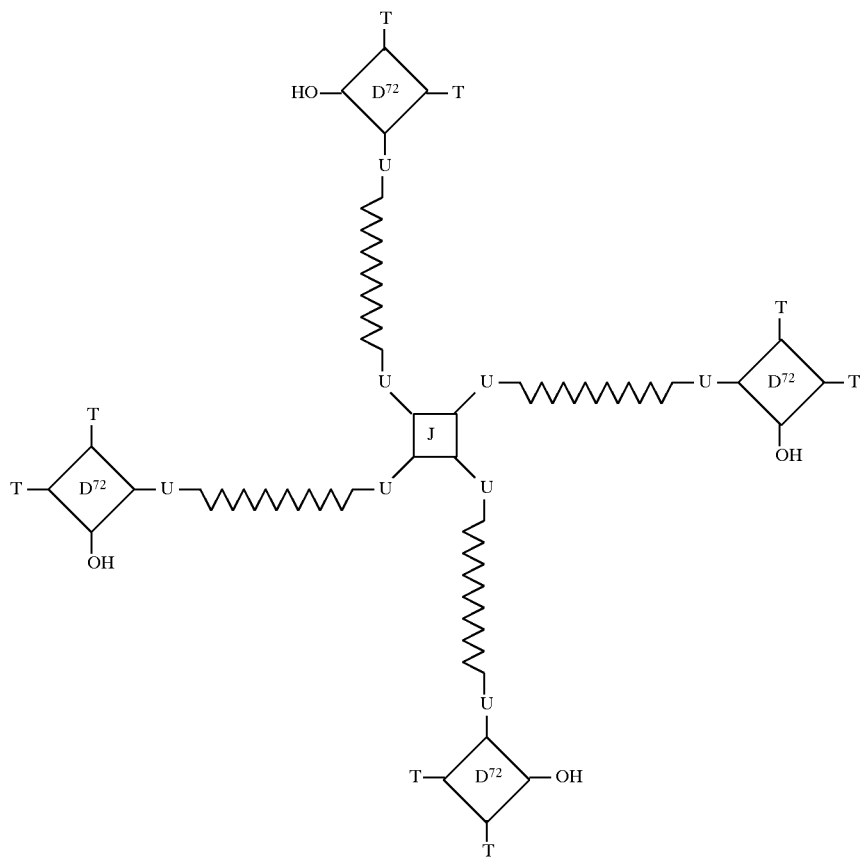

The properties of this composition are identified as "3A" in the table below. A second coating composition was prepared with a different drying package containing additional manganese component to increase through-dry. The characteristics of coating from this composition are identified as "3B" in the table.

A26.6 grams portion from the first beaker was mixed with a 47.2 gram portion of the product in the second beaker. The combination was heated to 80° C. and 2 drops dibutyl tin dilaurate and 1.1 grams isopropyldihsocyanate were added. The beaker then was placed in the 78° C. oven for two hours.

The resultant composition of the invention can be represented by the following structure:

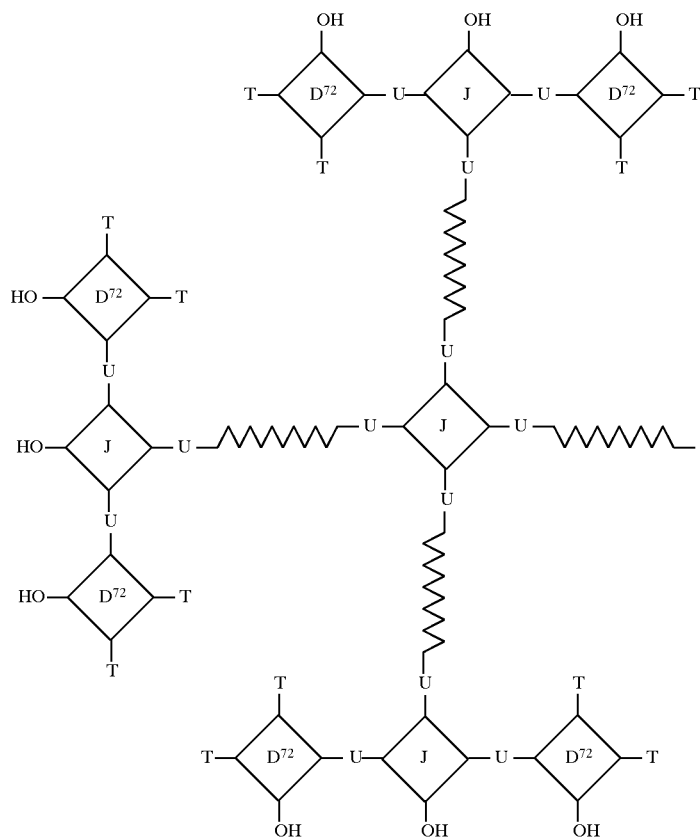

5. Coating System 7D5

Esterified composition of the invention of Part C of this example (22.3 grams), 11.8 grams of Composition J, 37.5 grams mineral spirits, and 2 drops dibutyl tin dilaurate were added to a beaker. The contents were heated to 90° C. to ensure dissolution, then cooled to 80° C. After mixing in 3.3 grams isophoronediisocyanate, the beaker was left in the 78° C. oven for two hours.

Then, 39.4 grams of this composition were mixed with 8.7 grams alkyd base, 24.9 grams mineral spirits, and 2 drops dibutyl tin dilaurate. After heating to 90° C. to ensure dissolution, the beaker was cooled to 80° C. and 1.8 grams isophoronediisocyanate were added. The beaker was left in the 78° C. oven for two hours.

The resulting composition of the invention can be represented in the following formula:

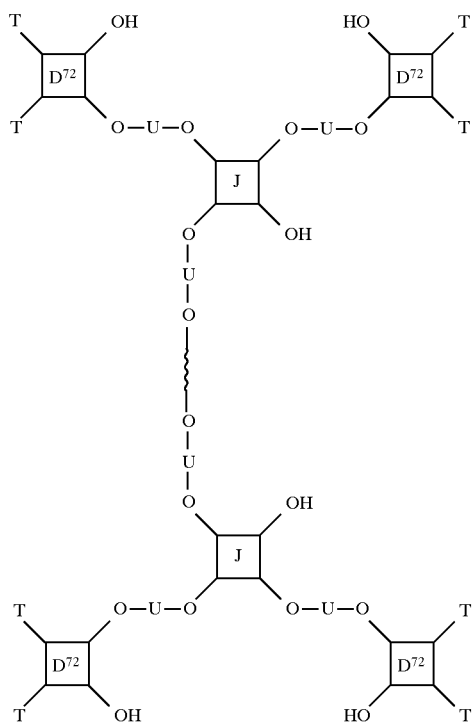

The following table summarizes the Sward Rocker hardness of plural tests of the compositions of the invention as set forth in this example at various time intervals after coating on steel Q panels using methods described above.

COATING PROPERTIES

| Hours | 1 | 2 | 3A | 4 | 3B | 5 |
|---|---|---|---|---|---|---|
| 24 | 16 | 18 | 4 | | | 33 |
| 48 | 20 | 18 | | | | 28 |
| 72 | | | | | | |
| 96 | | | 7 | 22 | 6 | |
| 120 | | 27 | 6 | 18 | 6 | |
| 144 | 24 | 22 | 5 | 23 | 8 | |
| 168 | 27 | 22 | 7 | 21 | 8 | |
| 192 | 28 | 20 | | | | |
| 216 | 31 | | | | | |

NOTE: All films were drawn as 2 mil wet films.

The data provided herein demonstrates that formaldehyde linked bisphenol-A systems styrenated with low cost styrene derivatives and alkoxylated with propylene carbonate can be derivatized with TOFA and other unsaturated fatty acids to produce additives capable of enhancing hardness and other performance attributes of alkyd-based coatings. These low cost systems are made possible through the esterification of the phenolic aralkylation polymers with TOFA and other fatty acids, which provides an unexpected solubility performance and related viscosity performance in non-polar environmentally friendly solvent systems such as mineral spirits.

The hardness data presented herein shown that uralkyd-modified versions of the aforementioned low cost TOFA-esterified phenolic aralkylation polymers typically produce coatings having Sward Rocker hardness greater than 20. Failure of the 7D3 system to show such high levels of hardness strongly suggests that the phenolic aralkylation polymers must be formed into higher molecular weight "star" polymer aggregates prior to grafting onto lower molecular weight alkyd systems. It also has been demonstrated that the grafting of alkyd resin components to these systems with diisocyanates results in systems showing very rapid hardness development as well as excellent scratch resistance and impact performance.

On a cost/performance basis, the low cost systems of the invention provide a substantial advantage over even TOFA systems of the invention produced with more expensive components.

Example 8 Various Alkyd and Uralkyd Preparations

A. Preparation of Linseed-Pentaerythritol Phthalic Anhydride Oxidizing Alkyd (Prior Art)

| Component | Reactor Charge, (grams) |
|---|---|
| Linseed Oil (First Grade) | 49.9 |
| Pentaerythritol | 8.6 |
| Lithium Hydroxide (alcoholysis catalyst) | 0.01 |
| Phthalic Anhydride | 17.1 |
| White Spirit Diluent | 24.5 |

A two-stage process was used with alcoholysis followed by polycondensation, using the fusion process technique.

1. Alcoholysis

The linseed oil, pentaerythritol, and lithium hydroxide were heated together under an inert gas atmosphere at 245–250° C. until a sample of the reaction mixture had a minimum tolerance of 25° C. when 1 part sample is added to 3 parts anhydrous methanol. This tolerance test requires that the material tested, i.e., the pentaerythritol/linseed oil product, does not form a second phase in the methanol/sample mixture.

2. Polycondensation

On completion of alcoholysis, the reaction mixture was cooled to 180° C. and phthalic anhydride added. The anhydride was allowed to react with the hydroxyl moiety of the reaction mixture for 30 minutes at 180° C. The reactants then were heated to 240° C. and held at this temperature, under an inert gas sweep, to remove o-xylene and water of condensation by azeotropic distillation. The course of the esterification was monitored by measurement of acid value and viscosity. The reaction was quenched by cooling to below 180° C. and diluting with mineral spirits, when the acid value was less than 10 mg KOH/g and the viscosity (measured at a temperature of 25° C. on a sample diluted to 75 percent in white spirit) reached between about 40–50 poise.

A series of Q panels was prepared from this prior art coating system at 70 percent solids and a dry-coat thickness of 0.5 mils after addition of appropriate dryer system (Co/Mn/Zr dryers are added). An average of Sward Rocker Hardness data for the panels are presented in the table at the end of this example.

FINAL PRIOR ART RESIN CHARACTERISTICS

| | |
|---|---|
| Color | 9 Gardner (maximum) |
| Viscosity at 25° C. | 40–60 poise (Gardner tubes $Z_2$–$Z_4$) |
| Acid value | 10 mg KOH/g (maximum) |
| Non-volatile content | 74–76 percent |
| Oil length* | 68 percent |

Note *-"Oil length" is the percent of fatty acid constituent in the coating solids.

B. Alkyd Coating System Comprising Linseed Oil, Pentaerythritol, Phthalic Anhydride, and Composition of the Invention G Composition of the Invention G, the formula for which is set forth above and reproduced below, was made in accordance with the methods set forth in Example 7.

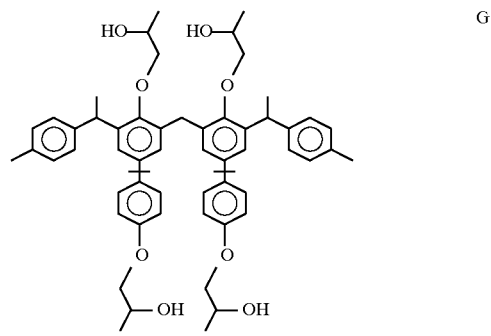

A two-stage process for making the alkyd coating system was used, with alcoholysis followed by polycondensation, using the fusion process technique. The following proportions of materials were used:

| Component | Reactor Charge, grams |
|---|---|
| Linseed Oil (First Grade) | 348.9 |
| Pentaerythritol | 30.1 |
| Lithium Hydroxide Monohydrate | 0.02 |
| Composition G | 207.2 |
| Phthalic Anhydride | 119.5 |

1. Alcoholysis

The linseed oil, Composition G, and lithium hydroxide were heated together under an inert gas atmosphere at 245–250° C. Alcoholysis was allowed to proceed for a period of two hours, at which time the pentaerythritol was added to the reaction mixture. The mixture was heated for an additional one hour or until the reaction mixture had a minimum tolerance at 25° C. of 1 part sample to 3 parts methanol.

2. Polycondensation

On completion of alcoholysis, the reaction mixture was cooled to 180° C. and phthalic anhydride added. The anhydride was allowed to react with the hydroxyl moiety of the reaction mixture for 30 minutes at 180° C. The reactants then were heated to 240° C. and held at this temperature, under an inert gas sweep, to remove o-xylene and water of condensation by azeotropic distillation. The course of the esterification was monitored by measurement of acid value and viscosity. The reaction was quenched by cooling to 180° C. and diluting with mineral spirits, when the acid value fell below 15 mg KOH/g and a viscosity (measured at a temperature of 25° C. on a sample diluted to 70 percent mineral spirits) of 40–50 poise was obtained.

A series of Q panels was prepared from this coating system of the invention at 70 percent solids after addition of appropriate dryer system (Co/Mn/Zr dryers are added). Data from the panels are presented in the table.

C. Alkyd Coating System Comprising Linseed Oil, Pentaerythritol, Phthalic Anhydride, and Composition of the Invention G The method of preparation was similar to that of Section B above, except the alcoholyses were carried out in separate reactors.

| Component | Total Reactor Charge, grams | |
|---|---|---|
| Linseed Oil (First Grade) | 348.9 | (split) |
| Pentaerythritol | 30.1 | |
| Lithium Hydroxide Monohydrate | 0.02 | |
| Composition of the Invention G | 207.2 | |
| Phthalic Anhydride | 119.5 | |

1. Alcoholyses

In one kettle, one-half of the linseed oil (174.5 grams) and 30.1 grams of pentaerythritol were co-reacted in the presence of the lithium hydroxide catalyst under an inert atmosphere at 245–250° C. until a sample of the reaction mixture had a minimum tolerance (i.e., produces a clear solution) at 25° C. of 1 part sample to 3 parts methanol. In a separate reactor, one-half of the linseed oil (174.5 grams) is reacted with 207.2 grams of composition of the invention G for two hours at a temperature of 245–250° C. Then, the contents of the pentaerythritol-containing reactor are transferred to the composition G-containing reactor.

2. Polycondensation

The reaction mixture was cooled to 180° C. and phthalic anhydride added. The reactor temperature was held at 180° C. for 30 minutes before heating to 240° C. The reactants were reacted at 240° C. under an inert gas sweep, with o-xylene solvent and the water of condensation removed by azeotropic distillation. Reaction was terminated when the final acid number was below 15 mg. KOH per gram. The remainder of the process was as described for Section A. After completion of the coating system, the appropriate dryer package was added and samples were drawn at a finished coating weight of 0.5 mils.

D. Alkyd Coating System Comprising Linseed Oil, Pentaerythritol, Phthalic Anhydride, and Composition of the Invention G The method of preparation of this example allows the linseed oil and Composition G to react with all the phthalic anhydride prior to addition of the linseed oil/pentaerythritol reaction mixture.

1. Alcoholysis

In one reactor, 174.5 grams of linseed oil and 207.2 grams of Composition G were reacted in the presence of the lithium hydroxide catalyst at 250° C. for three hours. At the end of this period, the reaction mixture was cooled to 160° C. and 119.5 grams of phthalic anhydride were added to the reaction mixture and allowed to react at 160° C. for 1 hour. In a second reactor, 174.5 grams of linseed oil was co-reacted with 30.1 grams of pentaerythritol in the presence of lithium hydroxide catalyst for 30–45 minutes until a 3:1 volume ratio of methanol to a sample of the reaction mixture produces a clear solution. The pentaerythritol containing reaction mixture then was added to the Composition G-containing reaction mixture.

2. Polycondensation

The reactants were reacted at 240° C. and held at this temperature under an inert gas sweep, with removal of the water of condensation and o-xylene removed by azeotropic distillation. The reaction was terminated when the final acid number was below 15 mg. KOH per gram. The remainder of the process was as described for Section A.

At the completion of the reaction, the coating system of the invention was diluted to 70 percent solids using mineral spirits. After addition of the standard dryer package, a series of panels was prepared at a dry coating thickness of 0.5 mils. Sward Rocker Hardness data for these panels are presented in the table below.

E. Incorporation of a "Star" Polymer of the Invention into a Linseed Oil Alkyd Polymer 1. Preparation of the "Star" Polymer The following were charged into a 400 ml beaker:

| Component | Percent of Total | Grams Charged |
|---|---|---|
| Composition of the Invention J | 23.1 | 11.5 |
| Composition of the Invention J Esterified with 2.5 TOFA | 66.5 | 33.2 |
| Isophoronediisocyanate | 10.4 | 5.2 |
| Mineral Spirits | | 50.0 |
| DABCO T-12 (polyurethane catalyst) | | 0.05 |

The reaction contents of the beaker were thoroughly mixed and was heated at 78° C. for a period of 90 minutes. Then 133 grams of a 75 percent solids linseed resin of Part A was added to the reaction mixture. Reaction was allowed to proceed for an additional 90 minutes at 78° C. The reaction then was allowed to stand for 24 hours at room temperature. Samples of the reaction mixture were drawn into coating films and it was observed that a slow-drying coating was produced. An additional 2 grams of isophoronediisocyanate were added to the reaction mixture, and the mixture was allowed to react at 78° C. for an additional 90 minutes. The resulting coating system was then diluted to 60 percent solids and an appropriate dryer package added. The resulting coating system was coated at 3 mils wet onto steel test panels. Sward Rocker hardness results are presented in the table below.

This coating system exhibits high hardness and abrasion resistance.

F. Prior Art Reduced Isophthalic Acid/Linseed Oil

COMPOSITION

| Component | Wt. in Charge (grams) | Molecular Wt. | Equivalent Wt. | Equivalence |
|---|---|---|---|---|
| Pentaerythritol | 86.1 | 136 | 34 | 2.53 |
| Linseed Oil | 498.5 | 872 | 290 | 1.71 |
| Phthalic Anhydride | 153 | 148 | 74 | 2.06 |

To a 1 liter rector fitted with a reflux decanter and a nitrogen sparge, 498 gms of linseed oil, 86.1 grams of pentaerythritol, and 0.1 gms of lithium hydroxide monohydrate were charged. The composition was heated to 250° C. under a nitrogen atmosphere. After heating for 1 hour at 250° C., a sample was taken and system was shown to form a clear solution when one part of the reaction mixture was mixed with three parts methanol.

Then, 153 grams of phthalic anhydride was charged to a reaction mixture, with the reaction temperature held at 180° C. for 30 minutes. Then, the system was heated at 250° C. under a blanket of inert gas with azeotropic distillation of o-xylene and the water of condensation.

After cooking for 4 hours, a carboxyl number of 2.9 was observed and the reaction was stopped. Mineral spirits (150 grams) was added to the reaction mixture together with 25.5 gms of isophoronediisocyanate and 0.2 gms of dibutyl tin dilaurate (polyurethane catalyst). The reaction was allowed to proceed for 90 minutes at 78° C. Samples of the reaction mixture were treated with an appropriate dryer package and drawn into a coating at 3 mils wet on steel plates. Sward Rocker hardness data are presented in the table.

G. Alkyd Coating System Comprising Pentaerythritol, Linseed Oil, Composition of the Invention G, and a Deficiency of Phthalic Anhydride The objective of this example was to produce a hydroxy-terminated phenolic aralkylation polymer/linseed oil-based/pentaerythritol alkyd.

| Component | Reactor Charge (grams) |
|---|---|
| Linseed Oil | 349.0 |
| Composition of the Invention G | 207.2 |
| Pentaerythritol | 30.1 |
| Phthalic Anhydride | 101.0 |
| Lithium Hydroxide Monohydrate | 0.2 |

Procedure:

A one-liter reactor was charged with 49.0 grams of linseed oil and 207.2 grams of Composition G. Also, 0.2 grams of lithium hydroxide monohydrate was charged as a catalyst. The reaction mixture was heated for 3 hours at 250° C. to allow the ester exchange reaction between the linseed oil and composition G. Then, 30.1 grams of pentaerythritol was added and the reaction was allowed to proceed for an additional 90 minutes at 250° C. The reactor then was cooled to 160° C. and 104.0 grams of phthalic anhydride were added to the reaction mixture along with 100 grams of o-xylene. The reaction was allowed to proceed at 150° C. for 30 minutes followed by reheating to 250° C. for eight hours to effect condensation of the polyester. At the end of that time, the final acid number was 7. The reaction mixture was stripped of the remaining o-xylene and 150 grams of mineral spirits was added. The reaction mixture then was heated and filtered through a 40 micron fritted glass porous plugged funnel and a sample was treated with appropriate dryer and drawn down on a steel test panel for physical evaluation. Sward Rocker hardness data are presented in the table below.

H. Coating System Comprising Composition of the Invention G, Linseed Oil, and a Deficiency of Phthalic Anhydride The objective of this example was to produce a hydroxy-terminated Composition G linseed oil-based alkyd suitable for finishing with a minimal quantity of a diisocyanate, such as isophoronediisocyanate.

REACTOR CRARGE

| Component | Reactor Charge (grams) |
|---|---|
| Linseed Oil | 198.5 |
| Composition of the Invention G | 242.6 |
| Phthalic Anhydride | 59.0 |
| Lithium Hydroxide Monohydrate | 0.1 |

Procedure:

A 1-liter reactor was charged with 198.5 grams of linseed oil and 242 grams of Composition G, with 0.1 grams of lithium hydroxide monohydrate added as a catalyst.

The reactor was heated to 250° C. and held for a period of 5 hours under o-xylene reflux. At that point, the reactor was cooled to 160° C. and 59.0 grams of phthalic anhydride were added with the temperature being held for 30 minutes before heating to 250° C. for five hours under o-xylene reflux. The carboxyl equivalent determination was 18. An aliquot was treated with an amount of isophoronediisocyanate equivalent to the phthalic anhydride deficiency. The treated aliquot then was diluted to 75 percent solids with mineral spirits and filtered while hot. A sample was treated with the standard dryer package and coatings were drawn at 3 mils wet on steel panels. Sward Rocker Hardness data are presented in the table below.

I. Coating System Comprising Composition of the Invention J and Product of Part D of this Example The Product of Part D of this example (72 grams) and Composition of the Invention J (25 grams) were added to a 400 ml beaker and heated to ensure dissolution. Mineral spirits (25 grams) then is added together with 3 grams of isophoronediisocyanate and 2 drops of dibutyl tin dilaurate. The reaction mixture then is heated for 120 minutes at 78° C. in a constant temperature oven. At the end of the period, a quantity of mineral spirits sufficient to reduce the solids concentration of the resultant coating resin to 50 wt percent. A dryer package is added.

Coatings were prepared on steel Q panels in accordance with standard preparation procedures.

The following mixtures of Compositions and products exemplified in this example also were prepared, with coatings prepared on steel Q panels in accordance with standard preparation procedures:

| Identifier | Composition, wt percent |
|---|---|
| 8J | Star Polymer of Example 8E |
| 8K | 33 Product of Example 8J, 67 Product of Example 8A |
| 8L | 50 Product of Example 8J, 50 Product of Example 8D |
| 8M | 70 Product of Example 8A, 30 Composition of the Invention G |

Hardness data for the compositions of this Example are set forth in the following table:

SWARD ROCKER HARDNESS (DOUBLE ROCKS)

| Product | Drying Time, Days | | | | |
|---|---|---|---|---|---|
| | 1 | 2 | 7 | 14 | 21 |
| 8A | 1 | 2 | 6 | 8 | |
| 8B | | 10 | 13 | 18 | |
| 8C | | | | | |
| 8D | | | 14 | 18 | |
| 8E | 12 | 15 | 21 | 26 | |
| 8F | 9 | 11 | 13 | | |
| 8G | 13 | 14 | | | |
| 8H | | 24 | | | |
| 8I | 22 | 23 | 26 | | |
| 8J | 22 | | 24 | | |
| 8K | 21 | | 24 | | |
| 8L | 22 | | 25 | | |
| 8M | | | 9 | 12 | |

Comparative Sward Rocker hardness, gloss, and back side impact data were obtained on the following coatings:

| | |
|---|---|
| Control | Behr SUPERSPAR ® spar varnish |
| Base | The Prior Art Product of Part 8A |
| Invention | Coating systems with selected portions of Composition of the Invention G replacing pentaerythritol of the Base system |

| System | 3 Day Sward | 7 Day Sward | 20 Gloss | 60 Gloss | 85 Gloss | Back side Impact (in-lb) |
|---|---|---|---|---|---|---|
| Control | 6 | 6 | 7.6 | 31.2 | 59.5 | 72 |
| Base | 2 | 3 | 88.2 | 89.5 | 76 | 132 |
| 25% | 9 | 13 | 110.5 | 107.7 | 95.2 | 128 |
| 50% | 7 | 11 | 106.4 | 108.2 | 91.6 | <4 |
| 75% | 10 | 16 | 103.5 | 105 | 94.7 | <4 |

The back side impact data shows that impact performance was maintained, even at 25 mole percent replacement of pentaerythritol by Composition G. For this sample, exterior stability is expected to be superior to that of the control, and color stability was improved. The other characteristics of these samples also compare favorably with the Base and Control coatings.

Example 9 Coating Systems Comprising Esterified 5-Functional Phenolic Polymer

A commercially available phenolic polymer of known composition was alkoxylated with ethylene carbonate in the presence of potassium hydroxide catalyst to form alkoxylated product in accordance with the following reaction:

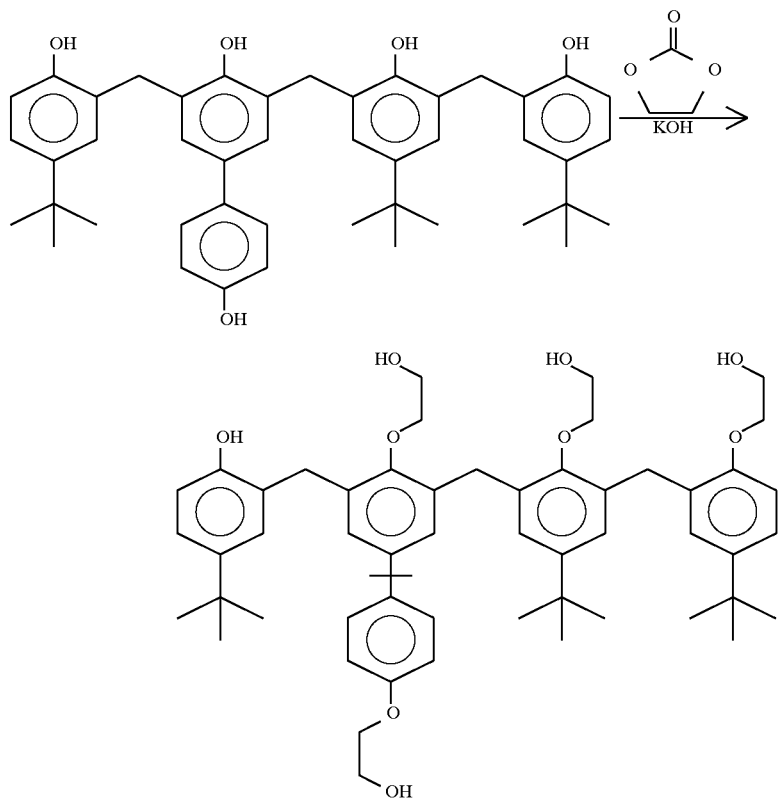

As can be seen, 4 of the 5 phenolic hydroxyl moieties were alkoxylated, as determined by NMR analysis.

The alkoxylated phenolic composition then was esterified with TOFA in quantity sufficient to esterify about 3 of the 4 aliphatic hydroxyl moieties to form esterified product, as follows:

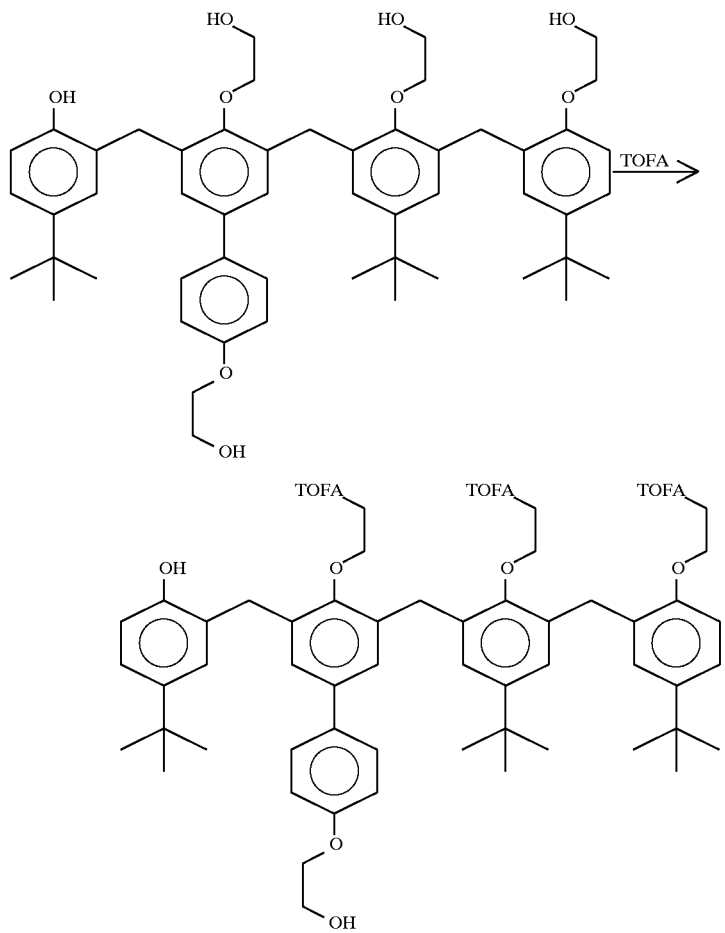

Two coating systems were made. In one, the esterified product of the example was used as an additive to an oil alkyd formulation. In the second system, an amount of the commercial phenolic polymer equal to the amount of esterified product was added to an otherwise identical oil alkyd formulation. An equal amount of a Co/Zr/Ca dryer package was used in each.

| System | 1 | 2 |
|---|---|---|
| Esterified Product, grams |  | 21.4 |
| Commercial Phenolic Polymer, grams | 21.4 |  |
| Oil Alkyd* | 134.2 | 134.2 |
| Mineral Spirit | 40 | 40 |
| Butanol | 5 | 5 |
| Properties |  |  |
| Brookfield Viscosity, cps | 4800 | 2200 |
| Color Number** | 28.1 | 3.1 |

Notes:
*McWorther Medium Oil Alkyd 5811
**From the L*a*b color coordinate measurements, converted to a percentage scale using non-coated panels as a standard An increase in color number indicates increasing color, with 100 being fully saturated yellow color and 0 being colorless. The color measurements were made using a Milton Roy ColorMate®/45 Color Analyzer. Measurements were made after 300 hours exposure of a coated steel Q panel in a Q-U-V® Accelerated Weathering Tester. Both the color number and the viscosity of the coating made from the coating system comprising a product of the invention are superior to those of the prior art.

It has been discovered that coating compositions of the invention exhibit properties superior to those of the prior art. For example, the prior art alkyd system of Example 8A, which was prepared from conventional alkyd starting materials using standard alkyd procedures, produced a coating system which has a high degree of scratch-resistance and toughness, but does not demonstrate a high Sward hardness. This failure to develop Sward hardness performance is somewhat due to the low initial molecular weight as well as the deficiency in the number of crosslinks. The linseed uralkyd of the invention, Example 8F1, produced by preparing the prior art system with 90 percent of the normal phthalic anhydride level and adding an isocyanate at a molar equivalent level to the phthalic anhydride deficiency, produced a system showing a slightly higher Sward Rocker hardness. This is believed to be attributable to the higher efficiency of the diisocyanate in producing crosslinks, which of course contribute to a higher degree of hardness development.

It has also been discovered that producing an alkyd with a diacid deficiency followed by finishing off with diisocyanate yields systems which exhibit higher degree of hardness, gloss, and much better performance, without requiring large amounts of diisocyanate. It is clear that isocyanate finishing of alkyds is an excellent way to achieve better coating performance. In addition, systems which are produced at an excess of hydroxy component exhibit lower final carboxyl numbers. A lower carboxyl number in the coating sample appears to be beneficial.

The inventors have discovered that 4-functional phenolic aralkylation polymers are readily ester-exchangeable with an oil, such as linseed oil, to produce fatty acid substituted, i.e., esterified, phenolic aralkylation polymers suitable for incorporation into alkyd and uralkyd coating systems. The secondary hydroxyls on the phenolic aralkylation polymers do require a longer period for transesterification. Incorporation of esterified phenolic aralkylation polymers into alkyd resins in addition to or in lieu of the conventional polyols such as pentaerythritol provide a high degree of aromaticity and hydrophobicity of these systems.

In particular, the inventors have discovered that 4-functional phenolic aralkylation polymers require no changes to methods of incorporation of known polyols. Thus, following the normal alkyd resin synthesis procedures leads to polymers having improved barrier performance and capable of achieving low carboxyl numbers, thus suggesting that the polymers of the invention have higher molecular weights.

It also has been discovered that ester exchange with isopropoxylated phenolic aralkylation polymer is slower than that observed with normal primary alcohols such as glycerol or pentaerythritol. However, when sufficient time is allowed for the ester exchange reaction, good results are obtained. In reactions where both pentaerythritol and a phenolic aralkylation polymer having 4 hydroxy functionalities are being reacted through an ester exchange with an oil such as linseed oil, it appears that it is advantageous to pre-react all of the linseed oil with the oil prior to reaction of the primary polyol. This procedure promotes an equal distribution between the true polyol components.

It appears that the largest benefit in terms of Sward Rocker hardness can be obtained by introduction of uralkyd drop-ins such as the Product of Example 8J. This material by itself has relatively poor mechanical performance; however, it does demonstrate a high immediate Sward Rocker hardness. It appears that the performance of this system, in terms of toughness and durability, is greatly increased by combining it with systems such as the base alkyd, i.e., the Product of Example 8A. Relatively low levels of the "drop-in"-type of composition appear to produce significant Sward Rocker hardness increases in the base linseed alkyd. It appears that the level of hardness development for the drop-in type systems, which are grafted with a small quantity of an isocyanate, is better than the systems which are produced by incorporation of the phenolic aralkylation polymer into the alkyd and uralkyd backbones. It appears that both grafting in as well as reaction in as a polyol component appear to be good ways to incorporate compositions of the invention to achieve increased hardness and other performance benefits.

The specification and the Examples describe, but do not limit, the invention, which is delimited only by the scope of the claims.

We claim:

1. An ester comprising the reaction product of a fatty acid with an aliphatic hydroxyl moiety of an alkoxylated phenolic aralkylation polymer comprising the alkoxylation reaction product of (1) an alkoxylating agent selected from the group consisting of alkylene oxides, alkylene carbonates, diene oxides, diene carbonates, glycerol carbonate, glycerol carbonate (meth)acrylate, glycidyl (meth)acrylate, lactones, and blends thereof with (2) a phenolic aralkylation polymer comprising the reaction product of a phenolic monomer having at least two free reactive positions; a styrene derivative; and a coupling agent.

2. The ester of claim 1 wherein the fatty acid is selected from the group consisting of TOFA, (meth)acrylic acid, and blends thereof; the phenolic monomer having at least two free reactive positions is selected from the group consisting of phenolic monomers containing mononuclear phenolic substituents, polyhydroxy mononuclear and polynuclear phenolic monomers, polynuclear phenolic monomers, and blends thereof; the styrene derivative is selected from the group consisting of styrene, α-methylstyrene, p-t-butylstyrene, m-ethylstyrene, p-ethylstyrene, p-vinyltoluene, mixed vinyltoluenes, mixed t-butylstyrenes, mixed ethylstyrenes, mixed t-butylstyrenes with di-t-butylstyrenes, or mixtures thereof; and the coupling agent is selected from the group consisting of aryl diolefins, formaldehyde, and blends thereof.

3. A chain-extended polyol comprising the alkoxylation product of (1) a non-esterified hydroxyl moiety of the ester of claim 1 with (2) a quantity of an alkylene oxide sufficient to provide a plurality of alkoxylation moieties per non-esterified hydroxyl moiety.

4. A chain-extended ester comprising the reaction product of (1) a fatty acid with (2) a chain-extended aliphatic hydroxyl moiety of the polyol of claim 3.

5. A chain-extended polyol comprising the alkoxylation product of (1) a hydroxyl moiety of a phenolic aralkylation polymer comprising the reaction product of a phenolic monomer having at least two free reactive positions; a styrene derivative; and a coupling agent, with (2) a quantity of an alkylene oxide sufficient to provide a plurality of alkoxylation moieties per non-esterified hydroxyl moiety.

6. An ester comprising the reaction product of a fatty acid with the chain-extended polyol of claim 5.

7. The ester of claim 6 wherein the fatty acid is selected from the group consisting of TOFA, (meth)acrylic acid, and blends thereof; the phenolic monomer having at least two free reactive positions is selected from the group consisting of phenolic monomers containing mononuclear phenolic substituents, polyhydroxy mononuclear and polynuclear phenolic monomers, polynuclear phenolic monomers, and blends thereof; the styrene derivative is selected from the group consisting of styrene, α-methylstyrene, p-t-butylstyrene, m-ethylstyrene, p-ethylstyrene, p-vinyltoluene, mixed vinyltoluenes, mixed t-butylstyrenes, mixed ethylstyrenes, mixed t-butylstyrenes with di-t-butylstyrenes, or mixtures thereof; and the coupling agent is selected from the group consisting of aryl diolefins, formaldehyde, and blends thereof.

8. An ester comprising the trans-esterification product of a glyceride oil with the chain-extended polyol of claim 5.

9. The ester of claim 8 wherein the glyceride oil is reactive oil; the phenolic monomer having at least two free reactive positions is selected from the group consisting of phenolic monomers containing mononuclear phenolic substituents, polyhydroxy mononuclear and polynuclear phenolic monomers, polynuclear phenolic monomers, and blends thereof; the styrene derivative is selected from the group consisting of styrene, α-methylstyrene, p-t-butylstyrene, m-ethylstyrene, p-ethylstyrene, p-vinyltoluene, mixed vinyltoluenes, mixed t-butylstyrenes, mixed ethylstyrenes, mixed t-butylstyrenes with di-t-butylstyrenes, or mixtures thereof; and the coupling agent is selected from the group consisting of aryl diolefins, formaldehyde, and blends thereof.

10. An ester comprising the transesterification product of a glyceride oil with an aliphatic hydroxyl moiety of an alkoxylated phenolic aralkylation polymer comprising the alkoxylation reaction product of (1) an alkoxylating agent selected from the group consisting of alkylene oxides, alkylene carbonates, diene oxides, diene carbonates, glycerol carbonate, glycerol carbonate (meth)acrylate, glycidyl (meth)acrylate, lactones, and blends thereof with (2) a phenolic aralkylation polymer comprising the reaction product of a phenolic monomer having at least two free reactive positions; a styrene derivative; and a coupling agent.

11. The ester of claim 10 wherein the glyceride oil is reactive oil; the phenolic monomer having at least two free reactive positions is selected from the group consisting of phenolic monomers containing mononuclear phenolic substituents, polyhydroxy mononuclear and polynuclear phenolic monomers, polynuclear phenolic monomers, and blends thereof; the styrene derivative is selected from the group consisting of styrene, α-methylstyrene, p-t-butylstyrene, m-ethylstyrene, p-ethylstyrene, p-vinyltoluene, mixed vinyltoluenes, mixed t-butylstyrenes, mixed ethylstyrenes, mixed t-butylstyrenes with di-t-butylstyrenes, or mixtures thereof; and the coupling agent is selected from the group consisting of aryl diolefins, formaldehyde, and blends thereof.

12. A chain-extended polyol comprising the alkoxylation product of (1) a non-esterified hydroxyl moiety of the ester of claim 8 with (2) a quantity of an alkylene oxide sufficient to provide a plurality of alkoxylation moieties per non-esterified hydroxyl moiety.

13. A chain-extended ester comprising the reaction product of (1) a fatty acid with (2) a chain-extended aliphatic hydroxyl moiety of the polyol of claim 12.

14. A diol ether polyol comprising the reaction product of glycerol carbonate with a phenolic hydroxyl moiety of a phenolic aralkylation polymer, the phenolic aralkylation polymer comprising the reaction product of a phenolic monomer having at least two free reactive positions; a styrene derivative; and a coupling agent.

15. An acrylate comprising the reaction product of an acrylate selected from the group consisting of glycerol carbonate (meth)acrylate, glycidyl (meth)acrylate, (meth)acrylic acid, and blends thereof, with a phenolic hydroxyl moiety of a phenolic aralkylation polymer, the phenolic aralkylation polymer comprising the reaction product of a phenolic monomer having at least two free reactive positions; a styrene derivative; and a coupling agent.

16. An ester comprising the reaction product of a lactone with a phenolic hydroxyl moiety of a phenolic aralkylation polymer, the phenolic aralkylation polymer comprising the reaction product of a phenolic monomer having at least two free reactive positions; a styrene derivative; and a coupling agent.

17. An epoxy comprising the reaction product of a difunctional epoxide selected from the group consisting of diglycidyl derivatives of bisphenol A and chain-extended derivatives thereof, aliphatic diepoxides based on the action of peracetic acid on cyclodiolefins, ester-linked cyclic diolefins, diglycidyl ethers of diols and of other diols formed by alkoxylation of diols, and blends thereof, with a hydroxyl moiety of a polymer selected from the group consisting of a phenolic aralkylation polymer having a hydroxyl functionality of at least 2, the phenolic aralkylation polymer comprising the reaction product of a phenolic monomer having at least two free reactive positions, a styrene derivative, and a coupling agent; a phenolic polymer having a hydroxyl functionality of at least 2, the phenolic polymer comprising the reaction product of a phenolic monomer having at least two free reactive positions and a styrene derivative, and blends thereof.

18. An acrylamide comprising the reaction product of an acrylamide selected from the group consisting of glycidyl (meth)acrylamide, glycidyl (meth)acrylamide carbonate, and blends thereof, with a hydroxyl moiety of a phenolic aralkylation polymer, the phenolic aralkylation polymer comprising the reaction product of a phenolic monomer having at least two free reactive positions; a styrene derivative; and a coupling agent.

19. The ester of claim 1 wherein the phenolic aralkylation polymer has a hydroxyl functionality of between about 4 and 10.

20. The ester of claim 1, wherein the ester has a hydroxyl functionality of less than about 2.

21. An alkoxylated phenolic aralkylation polymer polyol having a substituent having both hydroxyl and vinyl moieties pendant therefrom, said alkoxylated phenolic aralkylation polymer comprising the alkosylation product of (1) an oxirane- or carbonate ring-containing diene selected from the group consisting of diene oxide, diene carbonate, and blends thereof with (2) a phenolic hydroxyl moiety of a phenolic aralkylation polymer comprising the reaction product of a phenolic monomer having at least two free reactive positions; a styrene derivative; and a coupling agent.

22. An ester comprising the reaction product of (1) a fatty acid with (2) a pendant hydroxyl moiety of the alkoxylaated phenolic aralkylation polymer of claim 21.

23. A method for attaching a pendant carbonate moiety to an alkoxylated phenolic aralkylation polymer comprising grafting by free radical polymerization a diene carbonate to a methylene group in a position α to a phenolic ether on the alkoxylated phenolic aralkylation polymer.

24. An alkylene carbonate comprising the product of free radical polymerization of a diene carbonate to a methylene group in a position α to a phenolic ether on an alkoxylated phenolic aralkylation polymer.

25. A method for catalytically alkoxylating a composition having at least one hydroxyl moiety with an alkoxylating agent to form a product comprising an alkoxylation chain having at least one hydroxyl moiety pendant therefrom, said method comprising reacting an alkoxylating agent selected from the group consisting of alkylene oxides, alkylene carbonates, diene oxides, diene carbonates, glycerol carbonate, glycerol carbonate acrylate, glycidyl methacrylate, glycidyl acrylate, lactones, and blends thereof, with a hydroxyl moiety in the presence of a catalytically effective amount of guanidine carbonate.

26. The method of claim 25 wherein the alkoxylating agent is alkylene oxide and is present in an amount sufficient to provide a plurality of alkoxylating agents per hydroxyl moiety of the composition, thereby forming at least one extended chain by alkoxylation of hydroxyl moieties pendant from the alkoxylation chain.

27. An ester selected from the group consisting of

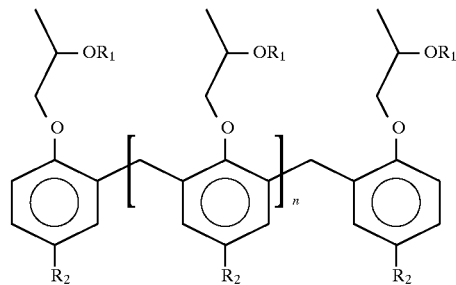

-continued

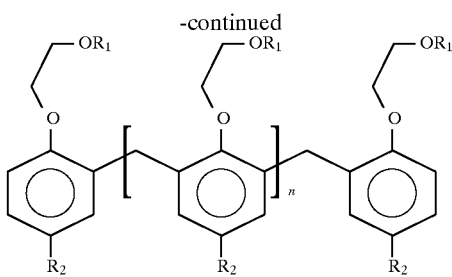

and blends thereof wherein n=1–10; each $R_1$ is separately selected from hydrogen and TOFA ester, with at least one $R_1$ being the ester; and each $R_2$ is separately selected from t-butyl and p-hydroxycumyl; and blends thereof.

28. An extended-chain phenolic aralkylation polymer comprising the reaction product of a chain-extending agent selected from the group consisting of dicarboxylic acids, polycarboxylic acids, dicarboxylic acid anhydrides, carboxyl acid anhydrides, diisocyanates, polyisocyanates, and blends thereof, with a non-esterified hydroxyl moiety of an ester selected from the group consisting of the ester of claim 1, the ester of claim 4, the ester of claim 6, the ester of claim 8, the ester of claim 10, the ester of claim 13, the ester of claim 16, the ester of claim 22, the ester of claim 27, and blends thereof.

29. The extended-chain phenolic aralkylation polymer of claim 28 wherein the non-esterified hydroxyl moiety of the ester is sequentially reacted first with a first chain-extending agent selected from the group consisting of dicarboxylic acids, polycarboxylic acids, dicarboxylic acid anhydrides, carboxylic acid anhydrides, and blends thereof, then with a second chain-extending agent selected from the group consisting of diisocyanates, polyisocyanates, and blends thereof.

30. A coating system comprising an ester selected from the group consisting of the ester of claim 1, the ester of claim 4, the ester of claim 6, the ester of claim 8, the ester of claim 10, the ester of claim 13, the ester of claim 16, the ester of claim 22, the ester of claim 27, and blends thereof.

31. A coating system comprising a polyol selected from the group consisting of the polyol of claim 3, the polyol of claim 5, the polyol of claim 12, the polyol of claim 14, the polyol of claim 21, and blends thereof.

32. A coating system comprising the acrylate of claim 15.

33. A coating system comprising the epoxy of claim 17.

34. A coating system comprising the acryamide of claim 18.

35. A coating system comprising the carbonate of claim 24.

36. A coating system comprising the polymer of claim 28.

* * * * *